US010366203B2

(12) United States Patent
Shaw

(10) Patent No.: US 10,366,203 B2
(45) Date of Patent: Jul. 30, 2019

(54) METHOD AND PROCEDURE TO FIND BEST FIT MEDICAL SERVICE PROVIDER

(71) Applicant: AT&T Intellectual Property I, L.P., Atlanta, GA (US)

(72) Inventor: Richard L. Shaw, Alpharetta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 593 days.

(21) Appl. No.: 14/922,631

(22) Filed: Oct. 26, 2015

(65) Prior Publication Data

US 2017/0116378 A1 Apr. 27, 2017

(51) Int. Cl.
| | | |
|---|---|---|
| G16H 10/60 | (2018.01) | |
| G16H 80/00 | (2018.01) | |
| G06F 19/00 | (2018.01) | |
| G01C 21/20 | (2006.01) | |
| G01C 21/34 | (2006.01) | |
| G01C 21/36 | (2006.01) | |

(52) U.S. Cl.
CPC .......... *G06F 19/328* (2013.01); *G01C 21/20* (2013.01); *G01C 21/3492* (2013.01); *G01C 21/3617* (2013.01); *G01C 21/3679* (2013.01); *G06F 19/32* (2013.01); *G16H 10/60* (2018.01); *G16H 80/00* (2018.01)

(58) Field of Classification Search
CPC ........ G16H 10/60; G16H 50/20; G16H 20/17; G16H 40/67; G16H 80/00; G16H 40/00
See application file for complete search history.

(56) References Cited

U.S. PATENT DOCUMENTS

| 6,970,827 | B2 | 11/2005 | Zeltzer et al. |
| 8,060,500 | B1 * | 11/2011 | Fitch ...................... G16H 40/20 |
| | | | 707/724 |
| 2007/0094044 | A1 | 4/2007 | Stone et al. |
| 2007/0136091 | A1 * | 6/2007 | McTaggart ............ G06F 19/327 |
| | | | 705/2 |
| 2008/0275741 | A1 | 11/2008 | Loeffen et al. |
| 2008/0300572 | A1 * | 12/2008 | Rankers ............. A61B 5/14532 |
| | | | 604/504 |
| 2009/0076855 | A1 * | 3/2009 | McCord ................ G06F 19/322 |
| | | | 705/3 |
| 2010/0070295 | A1 | 3/2010 | Kharraz Tavakol et al. |
| 2010/0070303 | A1 | 3/2010 | Massoumi et al. |
| 2011/0112858 | A1 * | 5/2011 | Neal ..................... G06F 19/327 |
| | | | 705/2 |
| 2011/0119079 | A1 | 5/2011 | Schoenberg |

(Continued)

*Primary Examiner* — Jonathan Durant
(74) *Attorney, Agent, or Firm* — BakerHostetler

(57) ABSTRACT

A method includes identifying a medical service for a user based on a request signal received from a mobile device associated with the user, the mobile device and identifying a plurality of medical service providers based on at least the medical service type. The method includes determining a plurality of travel times, wherein each of the plurality of travel times is indicative of a time to travel between the location and a provider location of a respective one of the plurality of service providers. The plurality of travel times are based on traffic information. The method also includes determining a ranking of the plurality of medical service providers based on the plurality of travel times and causing the mobile device to display at least a portion of the ranking.

15 Claims, 11 Drawing Sheets

(56) References Cited

U.S. PATENT DOCUMENTS

| | | | |
|---|---|---|---|
| 2011/0238288 A1* | 9/2011 | Li | G01C 21/3679 |
| | | | 701/533 |
| 2012/0123790 A1 | 5/2012 | Kenyon | |
| 2012/0215552 A1 | 8/2012 | Goldschmidt | |
| 2014/0012510 A1* | 1/2014 | Mensinger | G16H 40/40 |
| | | | 702/19 |
| 2014/0058739 A1 | 2/2014 | Guerra-Mondragon | |
| 2014/0172451 A1* | 6/2014 | Hudson | G06Q 10/10 |
| | | | 705/3 |
| 2014/0244275 A1 | 8/2014 | Parthasarathy | |
| 2014/0288957 A1 | 9/2014 | Grossman et al. | |
| 2014/0296659 A1* | 10/2014 | Lau | G06F 11/3013 |
| | | | 600/301 |

* cited by examiner

METHOD AND PROCEDURE TO FIND BEST FIT MEDICAL SERVICE PROVIDER

TECHNICAL FIELD

The technical field generally relates to location-based searching and, more specifically, to systems and methods for identifying emergency and urgent care service providers.

BACKGROUND

Many medical providers have limited operating hours or provided limited types of medical services. For afterhours medical care, many turn to the emergency room rather than search for an appropriate medical provider, even when the medical service needed does not constitute an emergency. However, there are often other options, such as urgent care and afterhours medical centers that can provide the same medical services. It may be difficult for a person to find a medical service provider that provides the medical service desired and is available to take patients in the near future. Even if afterhours medical care can be identified, patients often desire additional information about the afterhours medical center. For example, many afterhours medical centers provide a limited range of medical services. As another example, not all insurance plans are accepted at all medical centers. As yet another example, estimated wait times may instruct a person's choice in afterhours medical care. Further, the costs associated with the medical service from different service providers, including which insurance plans the service provider accepts, if any, may also be of interest to the person seeking treatment.

Often, the need for medical care is urgent, and the person seeking treatment may not have the luxury of time to research and identify a desired service provider. Thus, there is a need for a method and system for identifying medical service providers, particularly afterhours medical service providers.

SUMMARY

The disclosed systems and methods may allow for identifying medical service providers that provide a type of medical service and identifying from those medical providers, a preferred medical provider based on one or more of the cost, insurance plans accepted, the estimated wait time, the estimated arrival time, and the estimated treatment time.

According to one aspect, this disclosure is directed to a method that may include identifying a medical service for a user based on a request signal received from a mobile device associated with the user, the medical service having a type. The method may also include determining a location of the mobile device and identifying a plurality of medical service providers based on at least the medical service type. The method may also include determining a plurality of travel times, wherein each of the plurality of travel times is indicative of an estimated time to travel between the location and a provider location of a respective one of the plurality of medical service providers. The plurality of travel times are based on traffic information. The method may also include determining a ranking of the plurality of medical service providers based on the plurality of travel times and causing the mobile device to display at least a portion of the ranking.

According to another aspect, this disclosure is directed to a method that may include providing, via a user interface of a device, a control for requesting a medical service, the medical service having a type. The method may also include identifying a plurality of medical service providers, each of the plurality of medical service providers having an estimated wait time and a provider location service providers that provide the type of medical service requested based on a user input received via the control. Each of the plurality of each of the plurality of medical service providers having an estimated wait time and a provider location service providers may have an estimated wait time and a provider location. The method may also include determining a location of the device and, for each of the plurality of medical service providers, determining an estimated arrival time of the user based on at least the device location. The method may also include, for each of the plurality of medical service providers, estimating a treatment time based on at least one of the respective estimated arrival time and the respective estimated wait time The method may also include ranking the plurality of medical service providers based on the respective treatment times and providing, via the user interface, a list identifying at least a subset of the plurality of medical service providers. The ordering of the list may be based on the ranking.

According to yet another aspect, this disclosure is directed to a device that may include a processor and a communication system communicatively coupled to the processor. The device may also include a non-transitory memory comprising computer readable instructions that, when executed by the processor, cause the processor to effectuate operations. The operations may include, in response to receiving a medical request via the communication system from a user device, determining a location of the user device, the medical request indicative of a type of medical service. The method may also include, based on the user device location, identifying a plurality of medical service providers that provide the type of medical service requested, each of the plurality of medical service providers having an estimated wait time and a provider location. The method may include, for each of the plurality of medical service providers, determining an estimated travel time between the user device location and the provider location of the respective one of the plurality of medical service providers based on traffic data. The method may also include ranking the plurality of medical service providers based on at least the estimated wait times and the estimated travel times associated with each of the plurality of medical service providers.

BRIEF DESCRIPTION OF THE DRAWINGS

Aspects of the herein described telecommunications network are described more fully with reference to the accompanying drawings, which provide examples. In the following description, for purposes of explanation, numerous specific details are set forth in order to provide an understanding of the variations in implementing the disclosed technology. However, the instant disclosure may take many different forms and should not be construed as limited to the examples set forth herein. Acronyms are used throughout the disclosure that will be understood by those skilled in the art. Where practical, like numbers refer to like elements throughout.

DETAILED DESCRIPTION

Figure 1:
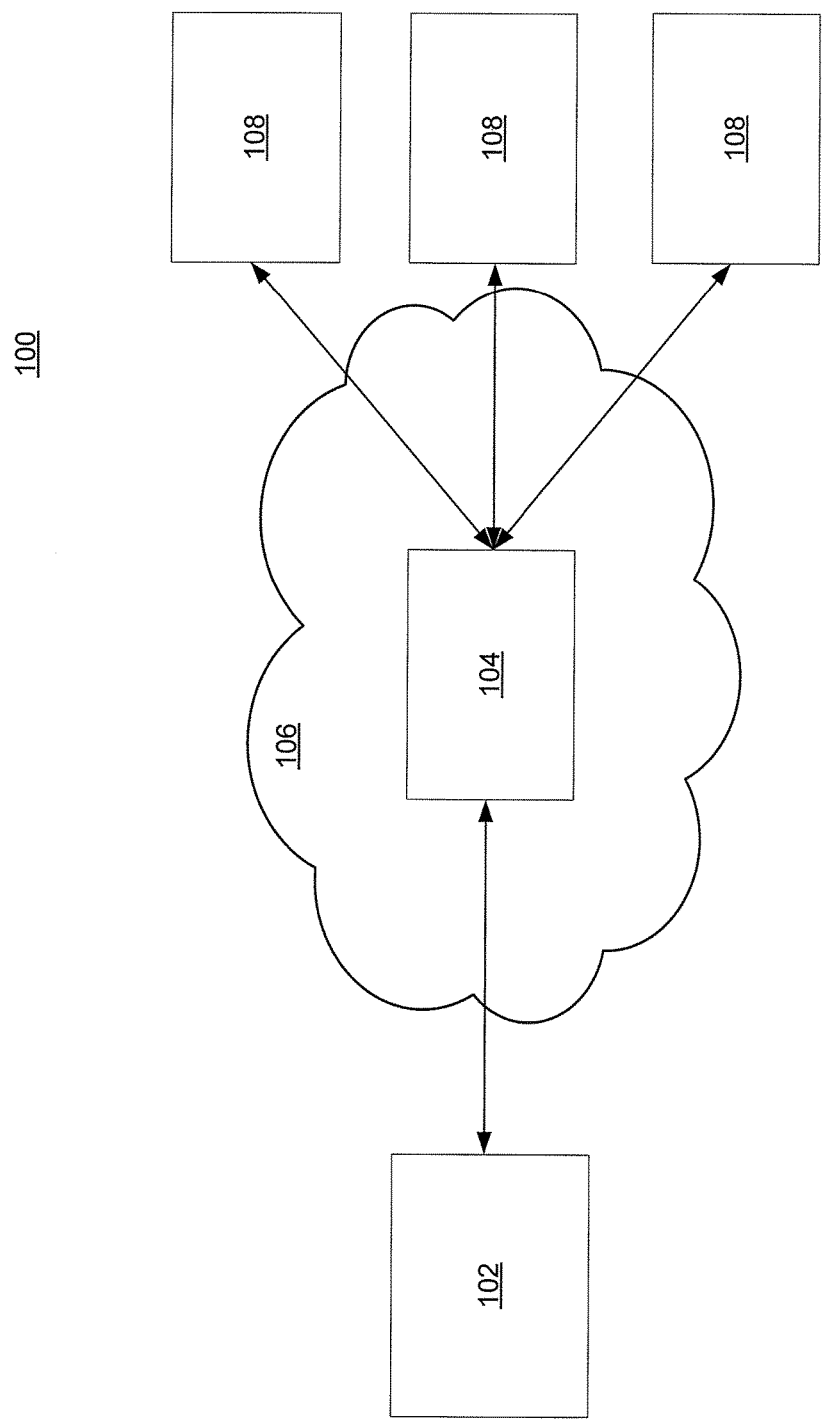
FIG. 1 illustrates an exemplary telecommunication system.

FIG. 1 illustrates an exemplary telecommunication system 100 including a mobile device 102 that may be associated with a user. In the context of the present disclosure, mobile device 102 may comprise any appropriate type of equipment, such as, for example, a computer, a server, a mobile phone, a tablet, or any type of equipment capable of transmitting data. Mobile device 102 may comprise a medical device, such as a wearable medical device or an embedded biometric monitoring device, that may monitor health characteristics. For example, mobile device 102 may be configured to transmit or record data based upon a certain condition of the health characteristics monitored. This data may include the data collected by monitoring the health characteristics. Additionally or alternatively, mobile device may transmit a request for medical service based upon the monitored health characteristics. Additionally or alternatively, mobile device 102 may be configured to transmit data in response to user input. It is to be understood that mobile device 102 as depicted herein is exemplary and not intended to be limiting.

Telecommunication system 100 may also include a network device 104 in communication with mobile device 102. Network device 104 may communicate through a network 106 that may comprise a subscriber network (e.g., long term evolution (LTE), 5G, etc.) or any other network (e.g., the internet). For example, network device 104 may communicate with one or more service providers 108. Network device 104 may include any device capable of communicating through subscriber network 106. For example, network device 104 may comprise a network entity. A network entity may comprise hardware or a combination of hardware and software. Network device 104 may include or constitute a component or various components of a cellular broadcast system wireless network, a processor, a server, a gateway, a node, a mobile switching center (MSC), a short message service center (SMSC), an ALFS, a gateway mobile location center (GMLC), a radio access network (RAN), a serving mobile location center (SMLC), or the like, or any appropriate combination thereof. Network device 104 may include, constitute, or be communicatively coupled to a mobile management entity (MME). Network device 104 may constitute a single device or multiple devices (e.g., single server or multiple servers, single gateway or multiple gateways, single controller or multiple controllers). Network device 104 may communicate wirelessly, via hard wire, or any appropriate combination thereof.

Medical service providers 108 may include any devices that are capable of communicating with other devices in telecommunication system 100, including network device 104. Medical service providers 108 may include or be associated with medical service personnel or practices, such as doctors, pharmacies, nurses, urgent care centers, or the like. Medical service providers 108 may be configured to transmit data, such as data related to medical service personnel or practices associated with medical service providers 108. For example, this data may include the types of medical services provided, the availability of medical services, operating hours, location(s), costs for services, accepted insurance plans, and estimated wait times. Data received form medical service providers 108 may be stored in a database of network device 102.

Figure 2:
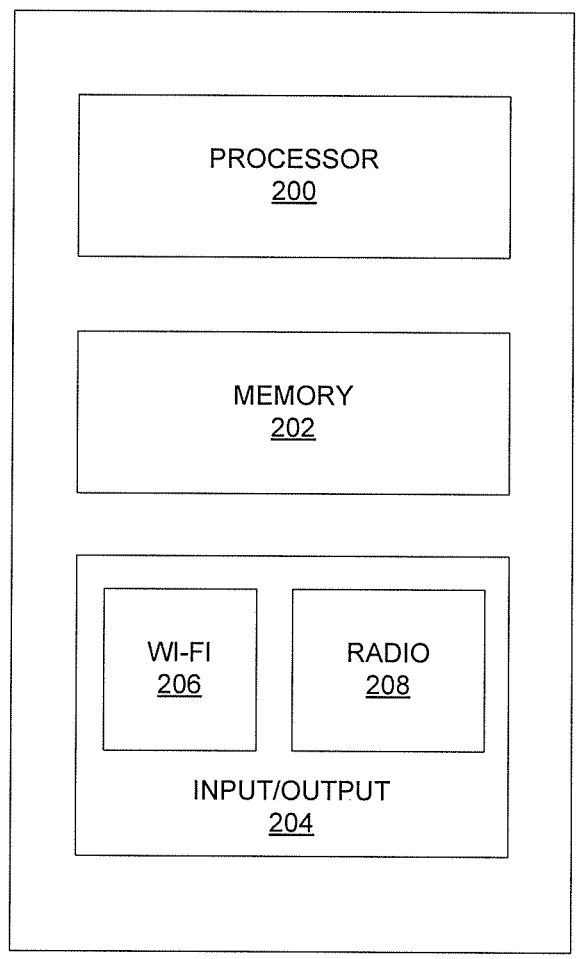
FIG. 2 is a schematic of an exemplary device that may transmit requests for medical service providers.

FIG. 2 is a block diagram of an exemplary mobile device 102 that may be utilized with a telecommunication network as described herein. Mobile device 102 may comprise or be incorporated into any appropriate device, including nonconventional devices like a kitchen appliance, a motor vehicle control (e.g., steering wheel), or the like. For example, any object or thing embedded with hardware or software to enable the thing to exchange data may constitute mobile device 102. Mobile device 102 may include devices across any industry. Mobile device 102 may be configured to communicate directly or indirectly with network device 104. Mobile device 102 may include appliances or things not found in traditional telecommunication systems, including sensors or monitors to detect heart rate, smoke, temperature, sound, pressure, water, humidity, movement, or the like or tracking devices affixed to living things or objects. Mobile device 102 may monitor health characteristics of one or more users, or it may be configured to monitor an environment or physical thing. For example, mobile device 102 may comprise a system configured to detect a car collision or the deployment of air bags. Mobile device 102 may be considered stationary or portable. As evident from the herein description, user equipment (UE), a device, a communications device, or a mobile device is not to be construed as software per se.

Mobile device 102 may include any appropriate device, mechanism, software, or hardware for communicating with a telecommunication network as described herein. In an example configuration, mobile device 102 may comprise portions including a processor 200, a memory 202, or an input/output 204. Each portion of mobile device 102 may comprise circuitry for performing functions associated with each respective portion. Thus, each portion may comprise hardware or a combination of hardware and software. Accordingly, each portion of mobile device 102 is not to be construed as software per se. It is emphasized that the block diagram depiction of mobile device 102 is exemplary and not intended to imply a specific implementation or configuration. For example, in an exemplary configuration, mobile device 102 may comprise a cellular communications technology, and processor 200 or memory 202 may be implemented, in part or in total, on a subscriber identity module (SIM) of mobile device 102. In another configuration, mobile device 102 may comprise a laptop computer. The laptop computer may include a SIM, and various portions of processor 200 or memory 202 may be implemented on the SIM, on the laptop other than the SIM, or any combination thereof.

Processor 200, memory 202, and input/output 204 may be coupled together (coupling not shown in FIG. 2) to allow communications therebetween. Input/output 204 may comprise a receiver of mobile device 102, a transmitter of mobile device 102, or a combination thereof. Input/output 204 may be capable of receiving or providing information pertaining to telecommunications as described herein. In various configurations, input/output 204 may receive or provide information via any appropriate means, such as, for example, optical means (e.g., infrared), electromagnetic means (e.g., radio frequency (RF), Wi-Fi, Bluetooth®, ZigBee®), acoustic means (e.g., speaker, microphone, ultrasonic receiver, ultrasonic transmitter), or a combination thereof. For example, as shown in FIG. 2, input/output 204 may include one or more wireless radios, such as Wi-Fi radio 206 or a radio 208. For example, input/output 204 may include one or more wireless radios dedicated to broadcast messages, for example, those receiving RF signals, such as a radio 208. As an example, input/output 204 may include one or more sensors, such as a biometric sensor or a personal health monitoring device. This may include, for example, a heart rate monitor, a blood pressure monitor, a blood glucose monitor, fitness trackers, weight monitors, sleep tracker, or any other type of sensor.

Processor 200 may be capable of performing functions pertaining to telecommunications, including, for example, communicating with other devices in or connected to network 106. In a basic configuration, mobile device 102 may include at least one memory 202, which may comprise executable instructions that, when executed by processor 200, cause processor 200 to effectuate operations associated with a telecommunication network, such as network 106. Memory 202 may comprise a storage medium having a concrete, tangible, physical structure. As is known, a signal does not have a concrete, tangible, physical structure. Memory 202, as well as any computer-readable storage medium described herein, is not to be construed as a transient signal. Further, memory 202, as well as any computer-readable storage medium described herein, is not to be construed as a propagating signal. Memory 202, as well as any computer-readable storage medium described herein, is to be construed as an article of manufacture.

Memory 202 may store any information utilized in conjunction with telecommunications. Depending upon the exact configuration or type of processor, memory 202 may be volatile (such as some types of RAM), nonvolatile (such as ROM or flash memory), or a combination thereof. Mobile device 102 may include additional storage (e.g., removable storage or nonremovable storage) including, but not limited to, tape, flash memory, smart cards, CD-ROM, DVD, or other optical storage, magnetic cassettes, magnetic tape, magnetic disk storage or other magnetic storage devices, universal serial bus (USB) compatible memory, or any other medium which can be used to store information and which can be accessed by mobile device 102.

Mobile device 102 may be used to receive or transmit messages through network 106 from a sender, such as another mobile device 102, network device 104, or medical service provider 108. It may be advantageous for mobile device 102 or another device in or connected to network 106 to communicate the location of mobile device 102 to network device 104, another mobile device 102, or medical service provider 108.

Figure 3:
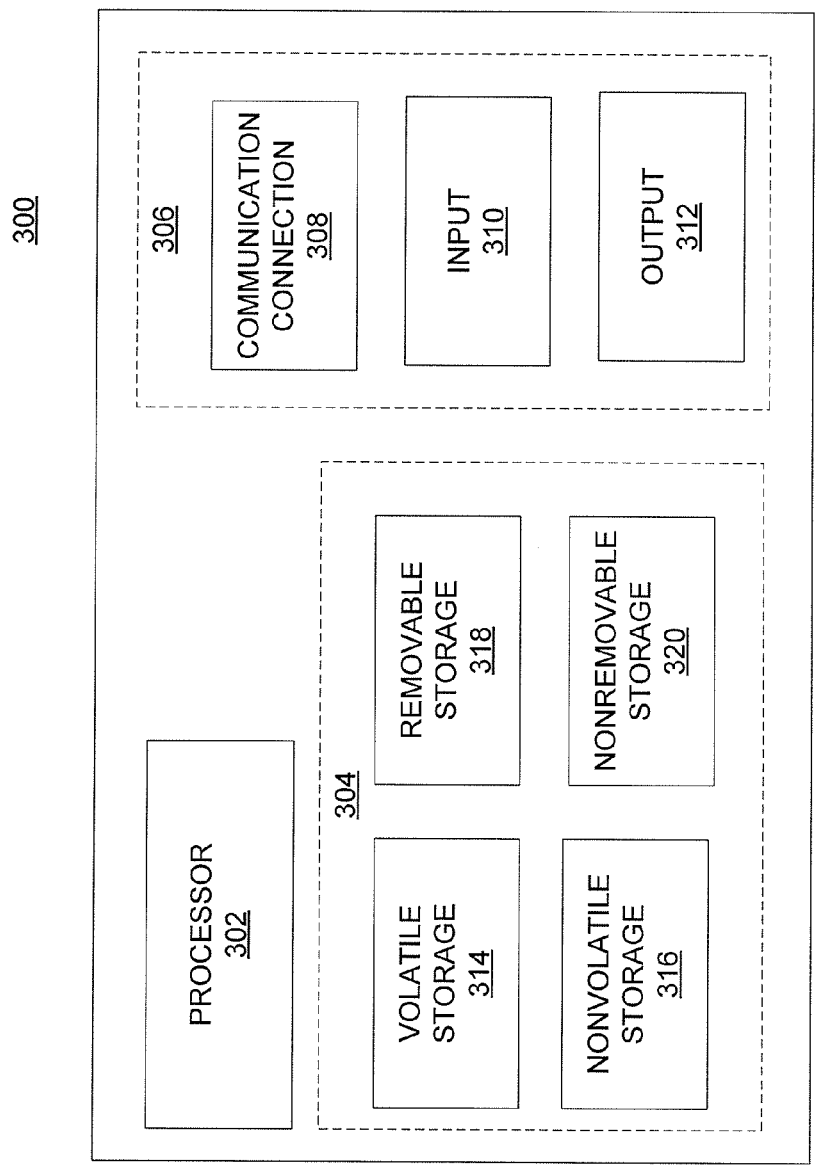
FIG. 3 is a schematic of an exemplary network entity.

FIG. 3 is a block diagram of network entity 300 of a telecommunication network (e.g., network 106) as described herein. For example, network device 104 may comprise, include, or communicate with network entity 300. Network entity 300 may comprise hardware or a combination of hardware and software. The functionality to facilitate telecommunications via a telecommunications network may reside in any one or combination of network entities 300.

Network entity 300 depicted in FIG. 3 may represent or perform functionality of any appropriate network entity 300 or combination of network entities 300, such as, for example, a component or various components of a cellular broadcast system wireless network, a processor, a server, a gateway, a node, a mobile switching center (MSC), a short message service center (SMSC), an ALFS, a gateway mobile location center (GMLC), a radio access network (RAN), a serving mobile location center (SMLC), or the like, or any appropriate combination thereof. It is emphasized that the block diagram depicted in FIG. 3 is exemplary and not intended to imply a specific implementation or configuration. Thus, network entity 300 may be implemented in a single device or multiple devices (e.g., single server or multiple servers, single gateway or multiple gateways, single controller or multiple controllers). Multiple network entities may be distributed or centrally located. Multiple network entities may communicate wirelessly, via hard wire, or any appropriate combination thereof.

Network entity 300 may comprise a processor 302 and a memory 304 coupled to processor 302. Memory 304 may contain executable instructions that, when executed by processor 302, cause processor 302 to effectuate operations associated with telecommunications via subscriber network 106. As evident from the description herein, network entity 300 is not to be construed as software per se.

In addition to processor 302 and memory 304, network entity 300 may include a communication system 306. Processor 302, memory 304, and communication system 306 may be coupled together (coupling not shown in FIG. 3) to allow communications therebetween. Each portion of network entity 300 may comprise circuitry for performing functions associated with each respective portion. Thus, each portion may comprise hardware, or a combination of hardware and software. Accordingly, each portion of network entity 300 is not to be construed as software per se. Communication system 306 may be capable of receiving or providing information from or to a communications device or other network entities configured for telecommunications. For example communication system 306 may include a wireless communications (e.g., 2.5G/3G/4G/GPS) card. Communication system 306 may be capable of receiving or sending video information, audio information, control information, image information, data, or any combination thereof. Communication system 306 may be capable of transferring information with network entity 300. In various configurations, communication system 306 may receive or provide information via any appropriate means, such as, for example, optical means (e.g., infrared), electromagnetic means (e.g., RF, Wi-Fi, Bluetooth®, ZigBee®), acoustic means (e.g., speaker, microphone, ultrasonic receiver, ultrasonic transmitter), or a combination thereof. In an example configuration, communication system 306 may comprise a Wi-Fi finder, a two-way GPS chipset or equivalent, or the like, or a combination thereof.

Communication system 306 of network entity 300 also may contain communication connection 308 that allows network entity 300 to communicate with other devices, network entities, or the like. Communication connection 308 may comprise communication media. Communication media typically embody computer-readable instructions, data structures, program modules or other data in a modulated data signal such as a carrier wave or other transport mechanism and includes any information delivery media. By way of example, and not limitation, communication media may include wired media such as a wired network or direct-wired connection, or wireless media such as acoustic, RF, infrared, or other wireless media. The term computer-readable media as used herein includes both storage media and communication media. Communication system 306 also may include an input device 310 such as keyboard, mouse, pen, voice input device, or touch input device. Communication system 306 may also include an output device 312, such as a display, speakers, or a printer.

Processor 302 may be capable of performing functions associated with telecommunications, such as functions for processing broadcast messages, as described herein. For example, processor 302 may be capable of, in conjunction with any other portion of network entity 300, determining a type of broadcast message and acting according to the broadcast message type or content, as described herein.

Memory 304 of network entity 300 may comprise a storage medium having a concrete, tangible, physical structure. As is known, a signal does not have a concrete, tangible, physical structure. Memory 304, as well as any computer-readable storage medium described herein, is not to be construed as a signal. Memory 304, as well as any computer-readable storage medium described herein, is not to be construed as a transient signal. Memory 304, as well as any computer-readable storage medium described herein, is not to be construed as a propagating signal. Memory 304, as well as any computer-readable storage medium described herein, is to be construed as an article of manufacture.

Memory 304 may store any information utilized in conjunction with telecommunications. Depending upon the exact configuration or type of processor, memory 304 may include a volatile storage 314 (such as some types of RAM), a nonvolatile storage 316 (such as ROM, flash memory), or a combination thereof. Memory 304 may include additional storage (e.g., a removable storage 318 or a nonremovable storage 320) including, for example, tape, flash memory, smart cards, CD-ROM, DVD, or other optical storage, magnetic cassettes, magnetic tape, magnetic disk storage or other magnetic storage devices, USB-compatible memory, or any other medium that can be used to store information and that can be accessed by network entity 300. Memory 304 may comprise executable instructions that, when executed by processor 302, cause processor 302 to effectuate operations to communicate via network 106.

Returning to FIG. 1, an exemplary implementation of telecommunication system 100 will be discussed. Network device 104 may be communicatively coupled to mobile device 102 and network 106. Network device 104 may receive a request signal from mobile device 102. The request signal may be indicative of a medical service requested by or for the user associated with mobile device 102. Network device 104 may determine a location of the mobile device 102. Based on the location, network device 104 may identify a plurality of medical service providers 108 that perform the medical service, such as by based on data stored in a database of network device 104. For example, network device 104 may store in a database information related to medical service providers 108. This information may be obtained from medical service providers 108 or from another source. For example, network device 104 may enable medical service providers 108 to register with network device 104. As part of this registration, medical service providers 108 may input certain information, such as insurance policies accepted, location(s), operating hours, contact information, a medical professional directory, services offered, or the like. In an aspect, medical service providers 108 may not have registered with network device 104. Rather, network device 104 may derive or obtain information related to unregistered medical service providers 108, such as from the Internet or other databases.

Network device 104 may identify a predefined number of the geographically closest medical service providers 108. For example, network device 104 may identify the closest twenty medical service providers 108 that perform the medical service. In another aspect, network device 104 may identify service providers within a predefined distance of the location of mobile device 102. For example, network device may identify medical service providers 108 within a five-mile radius, a thirty-minute walk, a thirty-minute drive, medical service providers 108 that are accessible by public transportation within ten miles or forty-five minutes, or the like. Network device 104 may determine an estimated travel time between the location of mobile device 102 and each of the plurality of medical service providers 108. The travel time may depend upon the mode of travel (e.g., by foot, by bike, by public transportation, by car). In an aspect, the mode of travel for each of medical service providers 108 may be the same. In another aspect, the means of travel for each of medical service providers 108 may vary. Additionally or alternatively, the estimated travel time may be based on traffic data. Based on the travel times, network device 104 may rank the plurality of service providers. For example, a medical service provider 108 that is within a ten-minute walk may be ranked higher than a medical service provider 108 that is closer, but is a twenty-minute drive due to heavy traffic. Other data may be used to determine the ranking of the plurality of medical service providers 108, including operating hours, estimated wait time, estimated arrival time, cost, the types of insurance accepted, the experience or qualifications of the medical personnel, customer ratings, or any other set of data. Network device 104 may cause mobile device 102 to display at least a portion of the ranking. For example, network device 104 may transmit data indicative of the ranking to mobile device 102, and mobile device 102 may render the ranking on a screen or other display.

Network device 104 may include one or more databases containing data relating to one or more medical service providers 108. Additionally or alternatively, network device 104 may receive data from one or more medical service providers 108 via network 106. For example, it may be possible to estimate how long a patient will have to wait before receiving treatment based on, for example, the number of patients already waiting, the number of medical professionals attending to patients, the types of medical services being provided, the length of appointments, or the like. Medical service provider 108 may be configured to autonomously and periodically transmit the estimated wait time to the network device 104. Additionally or alternatively, medical service provider 108 may provide data in response to a request from network device 104.

Figure 4:
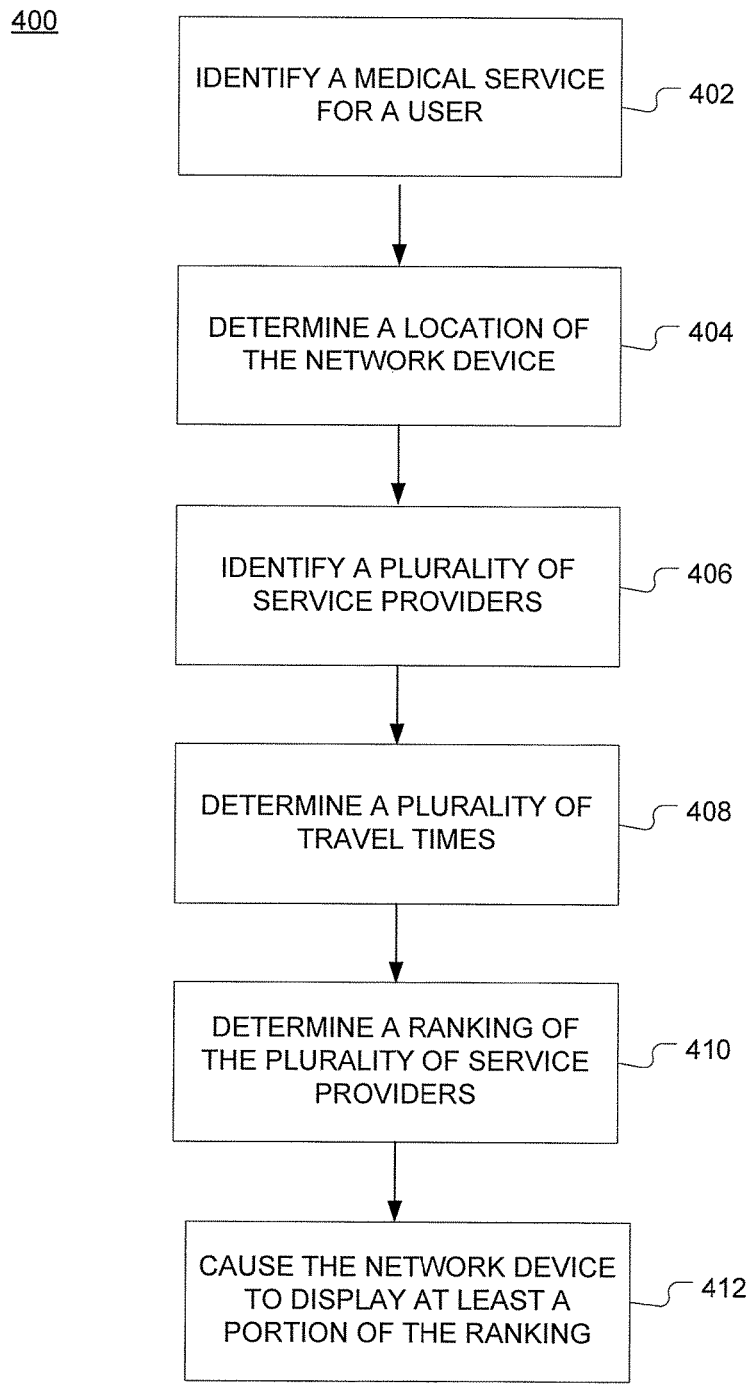
FIG. 4 is a flowchart of an exemplary process for identifying medical service providers based on traffic conditions.

FIG. 4 is a flowchart of an exemplary process 400 for identifying and ranking a plurality of medical service providers that provide the type of medical service the user desires. Process 400 may be implemented at least in part by network device 104, network entity 300, or a combination thereof. However, for simplicity, exemplary process 400 is described with reference to network device 104.

At step 402, network device 104 may identify a medical service for a user based on a request signal received from mobile device 102 associated with the user. The medical service may have a type. For example, the medical service may be treatment or diagnosis of a broken bone, an open wound, an infection, a virus, an injury sustained from an impact, such as a head injury or a back injury, a foreign object in the body (e.g., if a child swallowed a toy), a poisoning (e.g., a child ingested cleaning materials), an allergic reaction (e.g., anaphylactic shock), a mental health issue (e.g., a panic attack or suicidal behavior), an overdose, a cardiovascular condition (e.g., a heart attack), kidney stones, gall stones, bladder stones, appendicitis, an urgent issue of a chronic condition, a drug interaction, loss or imminent loss of consciousness, a seizure, or any other health condition or treatment.

For example, the request signal may indicate the type of medical care identified by the user. As another example, the request signal may be raw or processed data measured by a sensor of mobile device 102. For example, mobile device 102 may sense that a diabetic user's blood sugar level is in a dangerous range, and that the user's insulin pump is empty. In this example, the request signal could indicate a diabetes-related emergency or may include the raw data indicative of the blood sugar measurements. Thus, step 402 may include processing or analyzing data that constitutes the request signal to determine the type of medical service for the user. For example, if the blood sugar level is dangerously low, but not life-threatening, the medical service may comprise refilling a prescription for insulin with a nearby pharmacy. However, if the blood sugar levels indicate a life-threatening condition, the medical service may also include examination by a doctor or nurse practitioner.

As another example, the request signal may include a request or data input by the user of mobile device 102. For example, mobile device 102 may display a menu by which the user may select, highlight, or input symptoms or conditions. In an aspect, mobile device 102 may suggest symptoms. These suggestions may be based on data or conditions sensed by mobile device 104. For example, if mobile device 102 senses that a diabetic user's blood sugar level is low, a list of symptoms presented to the user may include faintness, light-headedness, or headache as possible symptoms. The user can confirm or deny that such symptoms are present. In another aspect, the user may input symptoms. In another aspect, the request signal may be based on the user input. For example, even if a blood-sugar sensor is not present, has not detected a condition needing medical attention, or is malfunctioning, mobile device 103 may still generate a request signal based on a user input. Similarly, the user input may include additional information about the condition, the user preferences, or the like, that can be used to identify appropriate healthcare providers.

At step 404, process 400 may include determining a location of mobile device 102. For example, network device 104 may receive location information from mobile device 102, such as GPS coordinates. Additionally or alternatively, the location may be determined using triangulation based on cell towers that can detect mobile device 102. As yet another example, location may be determined using trilateration based on WiFi signals.

At step 406, process 400 may include identifying a plurality of medical service providers 108 based on the type of the medical service. This may include identifying medical service providers 108 within a certain distance (e.g., a three-mile radius) or a certain travel time (e.g., within forty minutes). Step 406 may include identifying medical service providers 108 that provide or can provide the type of medical service indicated by the request signal. Process 400 may limit the plurality of medical service providers 108 to only those that are currently open, will be open within a certain amount of time, or that will remain open for a certain amount of time. For example, step 402 may include identifying medical service providers 108 that will be open for at least thirty minutes after the user is estimated to arrive. Additionally or alternatively, step 402 may include identifying medical service providers 108 that will be open within ten minutes of the user's arrival.

At step 408, process 400 may include determining a plurality of travel times. Each of the plurality of travel times may be associated with one of the plurality of medical service providers 108. Each of the plurality of travel times may be indicative of an estimated travel time from the location of mobile device 102 to the provider location of the respective medical service provider 108. Each of the plurality of travel times may be based on traffic information. For example, traffic information may be obtained based on location information of one or more network entities 300 connected to network 106. Additionally or alternatively, traffic information may include traffic reports or factor in current or imminent weather conditions, road conditions, or the like. As another example, the plurality of travel times may depend upon a mode of transportation (e.g., public transportation, car, walking, or biking).

At step 410, process 400 may include determining a ranking of the plurality of medical service providers 108. The ranking may be based on the plurality of travel times. The ranking may be based on estimated wait time associated with each of the plurality of medical service providers 108. For example, if the estimated wait time for medical service provider 108 is twenty-five minutes, and the travel time is twenty minutes, that service provider 108 may be ranked higher than one that is only ten minutes away but has a wait time of forty-five minutes. Ranking may further factor whether network device 104 can add the user to a schedule or waiting list for medical service provider 108. For example, if network device 104 is permitted to check in the user ahead of the user's arrival, this may speed up the user being attended to by a medical professional associated with medical service provider 108, which may impact the ranking.

The ranking may also factor in other information. For example, the ranking may exclude, or rank lower, medical service providers 108 that do not accept the insurance policy held by the user. Thus, process 400 may include identifying insurance plans accepted by each of the plurality of medical service providers 108 and identifying the health insurance plan associated with the user. Then, process 400 may include comparing the health insurance plans to the insurance plans accepted by each of the plurality of medical service providers 108. The ranking may exclude those medical service providers 108 that do not accept the user's health insurance plan. Additionally or alternatively, the display of the ranking may indicate those medical service providers 108 that do not accept the user's insurance policy such that the user can compare multiple medical service providers 108 based on the ranking, including whether they accept the user's insurance.

The ranking may also factor in ultimate cost of the medical service. For example, lower priced medical service provider 108 may be ranked higher than an otherwise comparable medical service provider 108 that charges more. The ranking may factor in the type of medical professional that will see the user. For example, the ranking may rank medical service provider 108 higher or lower depending on whether the user will see a nurse practitioner or a doctor. The ranking may depend on user ratings of medical service providers 108. This may include factoring in malpractice claims or official complaints against medical service providers 108. The ranking may be affected by the number of medical professionals at medical service provider 108.

The ranking may be based on preferences of the user. For example, medical service provider 108 that includes professionals that speak the user's native language may be ranked higher. Additionally or alternatively, the user may indicate a preference for female doctors. The preferences may indicate a requirement that the medical professional treat children. This may be advantageous, for example, if the user is scheduling a medical service for his child. The ranking may depend on whether medical service provider 104 will file with insurance, or whether the user is responsible for filing and seeking reimbursement from insurance. The ranking may depend on whether medical service provider 108 allows payment plans or accepts credit cards.

Step 410 may optionally include determining an estimated arrival time of the user at one or more of medical service providers 108. Further, process 400 may determine operating hours associated with each of the plurality of medical service providers 108. The ranking may be based on whether the estimated arrival time is within a predefined threshold of operating hours associated with a respective medical service provider 108. For example, if service provider 108 indicates a closing time that is only ten minutes later than the estimated arrival time of the user, that medical service provider 108 may be ranked lower or even excluded from the ranking.

At step 412, process 400 may include causing mobile device 102 to display at least a portion of the ranking. The display may be in any manner, including visual or audio. For example, the user may be able to review the list by scrolling. The list may include links to more information regarding a particular medical service provider 108. The display may also include controls by which the user can indicate a selection of a particular medical service provider 108. For example, network device 104 may use this selection to notify the medical service provider 108 in advance of the user's arrival. Network device 104 may optionally provide identifying information, such as contact information, medical history, current symptoms, type of medical service sought, or any other information to medical service provider 108. In instances where mobile device 102 that sent the request signal does not have a display, such as if mobile device 102 comprises a medical device configured to monitor a health characteristic, this step may include causing a different or separate component to display at least a portion of the ranking. For example, the ranking may be displayed on a user's mobile phone or tablet that also makes up mobile device 102.

Figure 5:
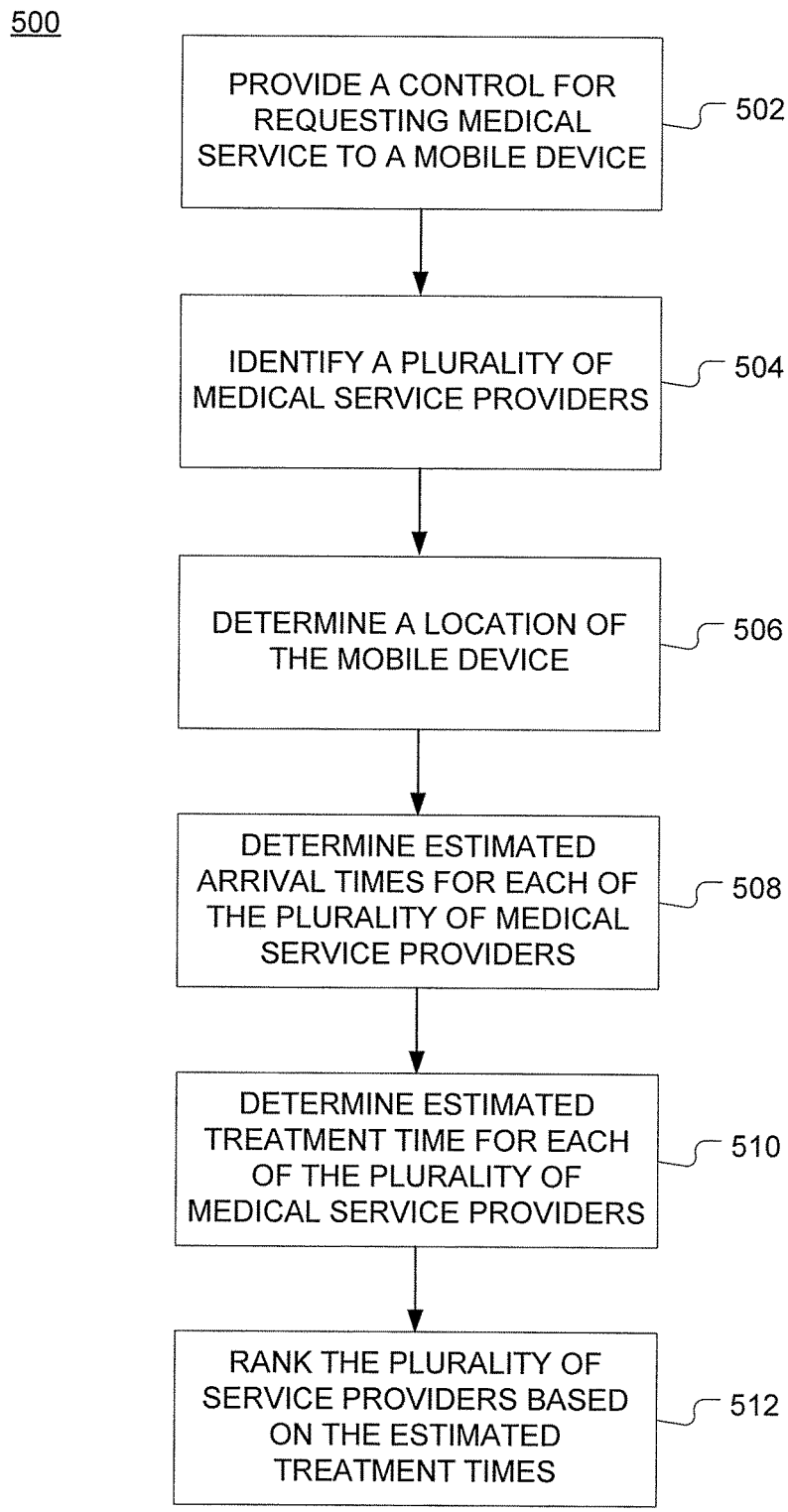
FIG. 5 is a flowchart of an exemplary process for identifying medical service providers based on traffic conditions.

FIG. 5 is a flowchart of an exemplary process 500. At step 502, process 500 may include providing, via a user interface of a device, such as input/output 204 of mobile device 200, a control for requesting a medical service. This control may be any time of user input, including a button displayed on screen, a soft button, or a hard button on mobile device 102. The control may be a trigger that may request a medical service if, for example, a certain condition occurs, such as a heart rate exceeding a predefined level.

At step 504, process 500 may include identifying a plurality of medical service providers 108 that provide the type of medical service requested based on the user input received via the control provided in step 502. Each of the plurality of medical service providers 108 may have an estimated wait time and a provider location. The user input, for example, could be a user setting that causes a trigger to trip based on a condition. Additionally or alternatively, the user input could be a user's audible command input through a microphone of input/output 204. The user input may indicate the type of medical service. Additionally or alternatively, the user input may indicate conditions or symptoms, and the type of medical service may be derived based on this information.

At step 506, process 500 may include determining a location of mobile device 104. This may be accomplished in any number of ways, such as querying mobile device 104, triangulating based on cell towers, triangulating based on Wi-Fi signals, GPS information, or user input.

At step 508, process 500 may include for each of the plurality of medical service providers 108, determining an estimated arrival time of the user based on at least the device location. The estimated arrival time may depend upon any number of factors, including, for example, a mode of transportation, traffic information, weather conditions, available routes, or any other information. For example, the mode of transportation may include factors such as a public transportation schedule, a vehicle route, a pedestrian route, or traffic information.

At step 510, process 500 may include for each of the plurality of service providers 108, estimating a treatment time based on the estimated arrival time or the estimated wait time. For example, step 510 may include determining whether a particular medical service provider 108 will accept a remote sign-in, such that the user is placed on the waiting list prior to arrival. If so, for example, and the current time is 12:05, the estimated arrival time is 12:40 and the estimated wait time is forty-five minutes, then the estimated treatment time may be 12:50. As another example, if the current time is 1:10, the estimated arrival time is 1:20, and the estimated wait time is twenty minutes, then the estimated treatment time may be 1:30.

At step 512, process 500 may include ranking the plurality of medical service providers 108 based on the estimated treatment time. This may include ranking medical service providers 108 from earliest estimated treatment time to the latest estimated treatment time. Additionally or alternatively, the estimated treatment time may be one of multiple factors on which the ranking is based.

Process 500 may include determining whether the operating hours of each of the plurality of medical service providers 108 for which the estimated arrival time is outside of a predetermined threshold of the operating hours of medical service provider 108. These medical service providers may comprise a first subset. For example, the predetermined threshold may include arrival times within 15 minutes of opening or 45 minutes of closing. Ranking medical service providers 108 may include excluding the first subset from the ranking.

Process 500 may include additional steps. For example, process 500 may include determining whether each of the plurality of medical service providers 108 accepts an insurance policy associated with the user or mobile device 102. The ranking, then, may be further based on which medical service providers 108, if any, accept the insurance policy.

Process 500 may include detecting a user input that is indicative of a user selection of a particular medical service provider 108. Process 500 may include providing a request for the medical service to the particular medical service provider 108. This may comprise providing a request for the medical service to a second device associated with the particular medical service provider 108. The request may include patient information associated with mobile device 102. Patient information may be a patient profile, contact information, description of symptoms, or medical history of user that is collected by network device 104 or entered by the user via mobile device 102. The request may indicate the user's estimated arrival time. This information may be used by medical service provider 108 to schedule treatment for the user.

Process 500 may include receiving a selection of one of the ranked plurality of medical service providers 108. Process 500 may also include providing travel directions from the location of mobile device 102 to a location of the selected one of the ranked plurality of medical service providers 108. For example, this may include providing turn-by-turn directions, or identifying the modes of public transportation that can be used to reach the selected medical service provider 108.

Figure 6:
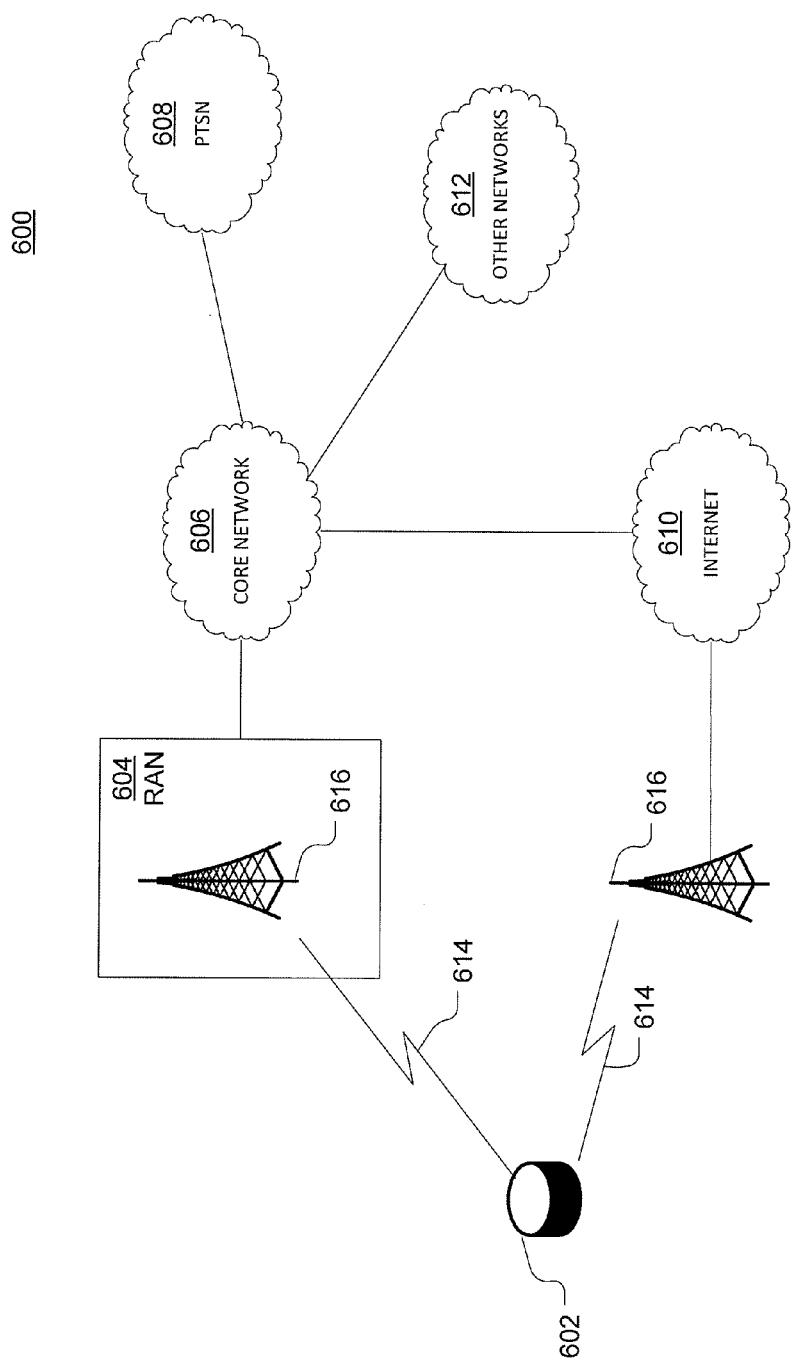
FIG. 6 is a diagram of an exemplary telecommunications system in which the disclosed methods and processes may be implemented.

As shown in FIG. 6, telecommunication system 600 may include wireless transmit/receive units (WTRUs) 602, a RAN 604, a core network 606, a public switched telephone network (PSTN) 608, the Internet 610, or other networks 612, though it will be appreciated that the disclosed examples contemplate any number of WTRUs, base stations, networks, or network elements. Each WTRU 602 may be any type of device configured to operate or communicate in a wireless environment. For example, a WTRU may comprise M2M device 108, a mobile device, network entity 300, or the like, or any combination thereof. By way of example, WTRUs 602 may be configured to transmit or receive wireless signals and may include a UE, a mobile station, a mobile device, a fixed or mobile subscriber unit, a pager, a cellular telephone, a PDA, a smartphone, a laptop, a netbook, a personal computer, a wireless sensor, consumer electronics, or the like. WTRUs 602 may be configured to transmit or receive wireless signals over an air interface 614.

Telecommunication system 600 may also include one or more base stations 616. Each of base stations 616 may be any type of device configured to wirelessly interface with at least one of the WTRUs 602 to facilitate access to one or more communication networks, such as core network 606, PTSN 608, Internet 610, or other networks 612. By way of example, base stations 616 may be a base transceiver station (BTS), a Node-B, an eNode B, a Home Node B, a Home eNode B, a site controller, an access point (AP), a wireless router, or the like. While base stations 616 are each depicted as a single element, it will be appreciated that base stations 616 may include any number of interconnected base stations or network elements.

RAN 604 may include one or more base stations 616, along with other network elements (not shown), such as a base station controller (BSC), a radio network controller (RNC), or relay nodes. One or more base stations 616 may be configured to transmit or receive wireless signals within a particular geographic region, which may be referred to as a cell (not shown). The cell may further be divided into cell sectors. For example, the cell associated with base station 616 may be divided into three sectors such that base station 616 may include three transceivers: one for each sector of the cell. In another example, base station 616 may employ multiple-input multiple-output (MIMO) technology and, therefore, may utilize multiple transceivers for each sector of the cell.

Base stations 616 may communicate with one or more of WTRUs 602 over air interface 614, which may be any suitable wireless communication link (e.g., RF, microwave, infrared (IR), ultraviolet (UV), or visible light). Air interface 614 may be established using any suitable radio access technology (RAT).

More specifically, as noted above, telecommunication system 600 may be a multiple access system and may employ one or more channel access schemes, such as CDMA, TDMA, FDMA, OFDMA, SC-FDMA, or the like.

For example, base station 616 in RAN 604 and WTRUs 602 connected to RAN 604 may implement a radio technology such as Universal Mobile Telecommunications System (UMTS) Terrestrial Radio Access (UTRA) that may establish air interface 614 using wideband CDMA (WCDMA). WCDMA may include communication protocols, such as High-Speed Packet Access (HSPA) or Evolved HSPA (HSPA+). HSPA may include High-Speed Downlink Packet Access (HSDPA) or High-Speed Uplink Packet Access (HSUPA). However, telecommunication system 600 is not limited to these exemplary technologies. Rather, telecommunication system 600 may include any telecommunication technology, including future protocols and the like. As another example base station 616 and WTRUs 602 that are connected to RAN 604 may implement a radio technology such as Evolved UMTS Terrestrial Radio Access (E-UTRA), which may establish air interface 614 using LTE or LTE-Advanced (LTE-A).

Optionally base station 616 and WTRUs 602 connected to RAN 604 may implement radio technologies such as IEEE 602.16 (i.e., Worldwide Interoperability for Microwave Access (WiMAX)), CDMA2000, CDMA2000 1×, CDMA2000 EV-DO, Interim Standard 2000 (IS-2000), Interim Standard 95 (IS-95), Interim Standard 856 (IS-856), GSM, Enhanced Data rates for GSM Evolution (EDGE), GSM EDGE (GERAN), or the like.

Base station 616 may be a wireless router, Home Node B, Home eNode B, or access point, for example, and may utilize any suitable RAT for facilitating wireless connectivity in a localized area, such as a place of business, a home, a vehicle, a campus, or the like. For example, base station 616 and associated WTRUs 602 may implement a radio technology such as IEEE 602.11 to establish a wireless local area network (WLAN). As another example, base station 616 and associated WTRUs 602 may implement a radio technology such as IEEE 602.15 to establish a wireless personal area network (WPAN). In yet another example, base station 616 and associated WTRUs 602 may utilize a cellular-based RAT (e.g., WCDMA, CDMA2000, GSM, LTE, LTE-A, etc.) to establish a picocell or femtocell. As shown in FIG. 6, base station 616 may have a direct connection to Internet 610. Thus, base station 616 may not be required to access Internet 610 via core network 606.

RAN 604 may be in communication with core network 606, which may be any type of network configured to provide voice, data, applications, and/or voice over internet protocol (VoIP) services to one or more WTRUs 602. For example, core network 606 may provide call control, billing services, mobile location-based services, pre-paid calling, Internet connectivity, video distribution or high-level security functions, such as user authentication. Although not shown in FIG. 6, it will be appreciated that RAN 604 or core network 606 may be in direct or indirect communication with other RANs that employ the same RAT as RAN 604 or a different RAT. For example, in addition to being connected to RAN 604, which may be utilizing an E-UTRA radio technology, core network 606 may also be in communication with another RAN (not shown) employing a GSM radio technology.

Core network 606 may also serve as a gateway for WTRUs 602 to access PSTN 608, Internet 610, or other networks 612. PSTN 608 may include circuit-switched telephone networks that provide plain old telephone service (POTS). For LTE core networks, core network 606 may use IMS core 614 to provide access to PSTN 608. Internet 610 may include a global system of interconnected computer networks or devices that use common communication protocols, such as the transmission control protocol (TCP), user datagram protocol (UDP), or IP in the TCP/IP internet protocol suite. Other networks 612 may include wired or wireless communications networks owned or operated by other service providers. For example, other networks 612 may include another core network connected to one or more RANs, which may employ the same RAT as RAN 604 or a different RAT.

Some or all WTRUs 602 in telecommunication system 600 may include multi-mode capabilities. That is, WTRUs 602 may include multiple transceivers for communicating with different wireless networks over different wireless links. For example, one or more WTRUs 602 may be configured to communicate with base station 616, which may employ a cellular-based radio technology, and with base station 616, which may employ an IEEE 802 radio technology.

Figure 7:
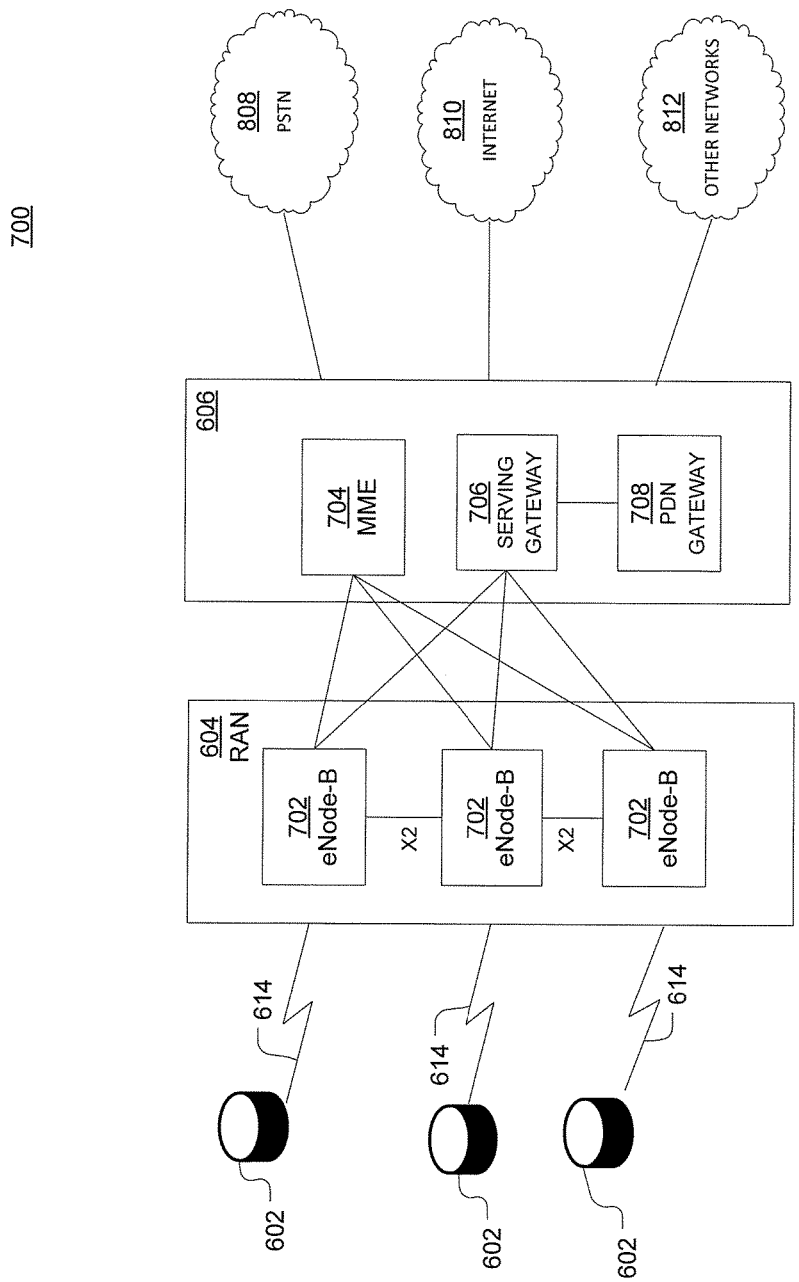
FIG. 7 is an example system diagram of a radio access network and a core network.

FIG. 7 is an example system 700 including RAN 604 and core network 606. As noted above, RAN 604 may employ an E-UTRA radio technology to communicate with WTRUs 602 over air interface 614. RAN 604 may also be in communication with core network 606.

RAN 604 may include any number of eNode-Bs 702 while remaining consistent with the disclosed technology. One or more eNode-Bs 702 may include one or more transceivers for communicating with the WTRUs 602 over air interface 614. Optionally, eNode-Bs 702 may implement MIMO technology. Thus, one of eNode-Bs 702, for example, may use multiple antennas to transmit wireless signals to, or receive wireless signals from, one of WTRUs 602.

Each of eNode-Bs 702 may be associated with a particular cell (not shown) and may be configured to handle radio resource management decisions, handover decisions, scheduling of users in the uplink or downlink, or the like. As shown in FIG. 7 eNode-Bs 702 may communicate with one another over an X2 interface.

Core network 606 shown in FIG. 7 may include a mobility management gateway or entity (MME) 704, a serving gateway 706, or a packet data network (PDN) gateway 708. While each of the foregoing elements are depicted as part of core network 606, it will be appreciated that any one of these elements may be owned or operated by an entity other than the core network operator.

MME 704 may be connected to each of eNode-Bs 702 in RAN 604 via an S1 interface and may serve as a control node. For example, MME 704 may be responsible for authenticating users of WTRUs 602, bearer activation or deactivation, selecting a particular serving gateway during an initial attach of WTRUs 602, or the like. MME 704 may also provide a control plane function for switching between RAN 604 and other RANs (not shown) that employ other radio technologies, such as GSM or WCDMA.

Serving gateway 706 may be connected to each of eNode-Bs 702 in RAN 604 via the S1 interface. Serving gateway 706 may generally route or forward user data packets to or from the WTRUs 602. Serving gateway 706 may also perform other functions, such as anchoring user planes during inter-eNode B handovers, triggering paging when downlink data is available for WTRUs 602, managing or storing contexts of WTRUs 602, or the like.

Serving gateway 706 may also be connected to PDN gateway 708, which may provide WTRUs 602 with access to packet-switched networks, such as Internet 610, to facilitate communications between WTRUs 602 and IP-enabled devices.

Core network 606 may facilitate communications with other networks. For example, core network 606 may provide WTRUs 602 with access to circuit-switched networks, such as PSTN 608, such as through IMS core 614, to facilitate communications between WTRUs 602 and traditional landline communications devices. In addition, core network 606 may provide the WTRUs 602 with access to other networks 612, which may include other wired or wireless networks that are owned or operated by other service providers.

Figure 8:
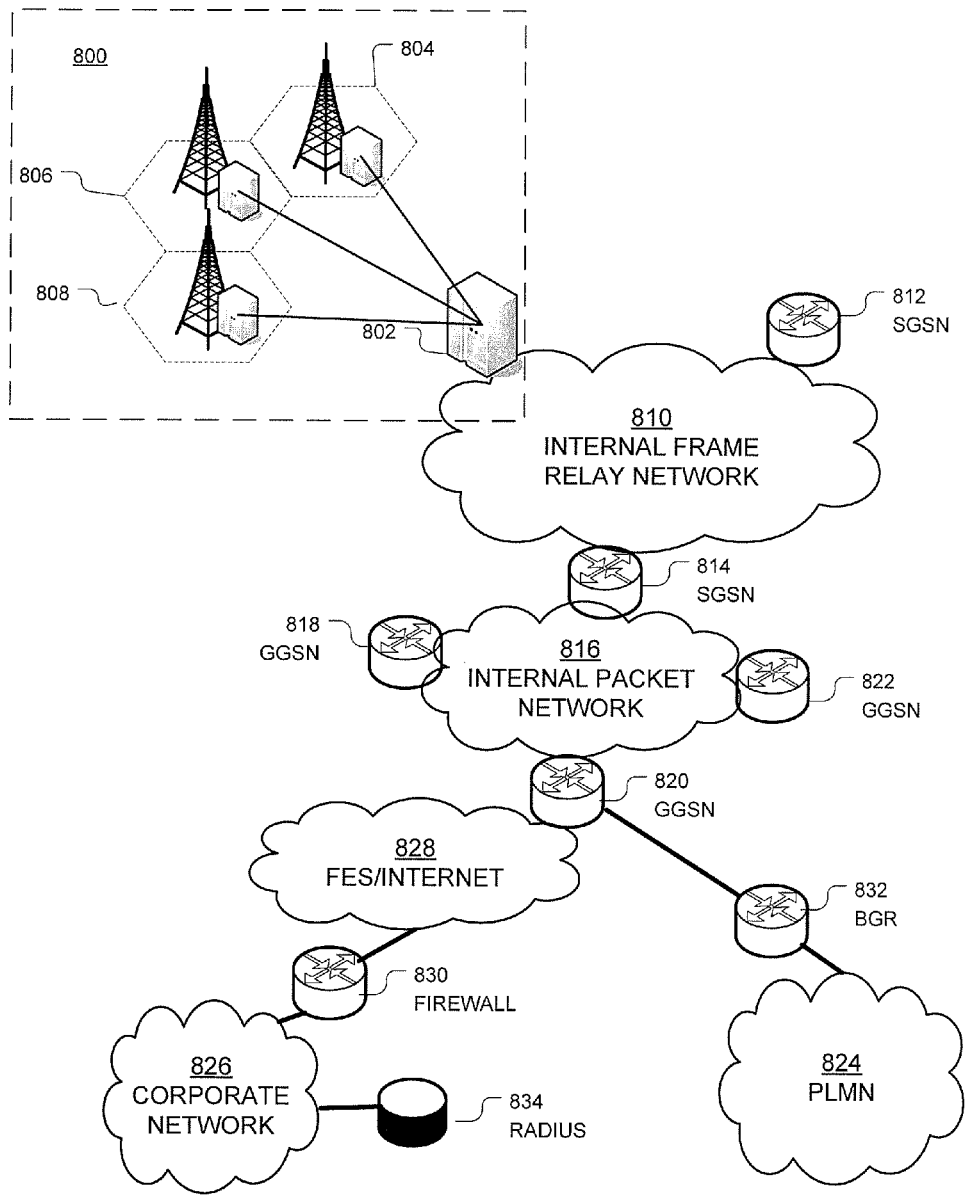
FIG. 8 depicts an overall block diagram of an example packet-based mobile cellular network environment, such as a general packet radio service (GPRS) network.

FIG. 8 depicts an overall block diagram of an example packet-based mobile cellular network environment, such as a GPRS network as described herein. In the example packet-based mobile cellular network environment shown in FIG. 8, there are a plurality of base station subsystems (BSS) 800 (only one is shown), each of which comprises a base station controller (BSC) 802 serving a plurality of BTSs, such as BTSs 804, 806, 808. BTSs 804, 806, 808 are the access points where users of packet-based mobile devices become connected to the wireless network. In example fashion, the packet traffic originating from mobile devices is transported via an over-the-air interface to BTS 808, and from BTS 808 to BSC 802. Base station subsystems, such as BSS 800, are a part of internal frame relay network 810 that can include a service GPRS support nodes (SGSN), such as SGSN 812 or SGSN 814. Each SGSN 812, 814 is connected to an internal packet network 816 through which SGSN 812, 814 can route data packets to or from a plurality of gateway GPRS support nodes (GGSN) 818, 820, 822. As illustrated, SGSN 814 and GGSNs 818, 820, 822 are part of internal packet network 816. GGSNs 818, 820, 822 mainly provide an interface to external IP networks such as PLMN 824, corporate intranets/internets 826, or Fixed-End System (FES) or the public Internet 828. As illustrated, subscriber corporate network 826 may be connected to GGSN 820 via a firewall 830. PLMN 824 may be connected to GGSN 820 via a boarder gateway router (BGR) 832. A Remote Authentication Dial-In User Service (RADIUS) server 834 may be used for caller authentication when a user calls corporate network 826.

Generally, there may be a several cell sizes in a GSM network, referred to as macro, micro, pico, femto or umbrella cells. The coverage area of each cell is different in different environments. Macro cells can be regarded as cells in which the base station antenna is installed in a mast or a building above average roof top level. Micro cells are cells whose antenna height is under average roof top level. Micro cells are typically used in urban areas. Pico cells are small cells having a diameter of a few dozen meters. Pico cells are used mainly indoors. Femto cells have the same size as pico cells, but a smaller transport capacity. Femto cells are used indoors, in residential or small business environments. On the other hand, umbrella cells are used to cover shadowed regions of smaller cells and fill in gaps in coverage between those cells.

Figure 9:
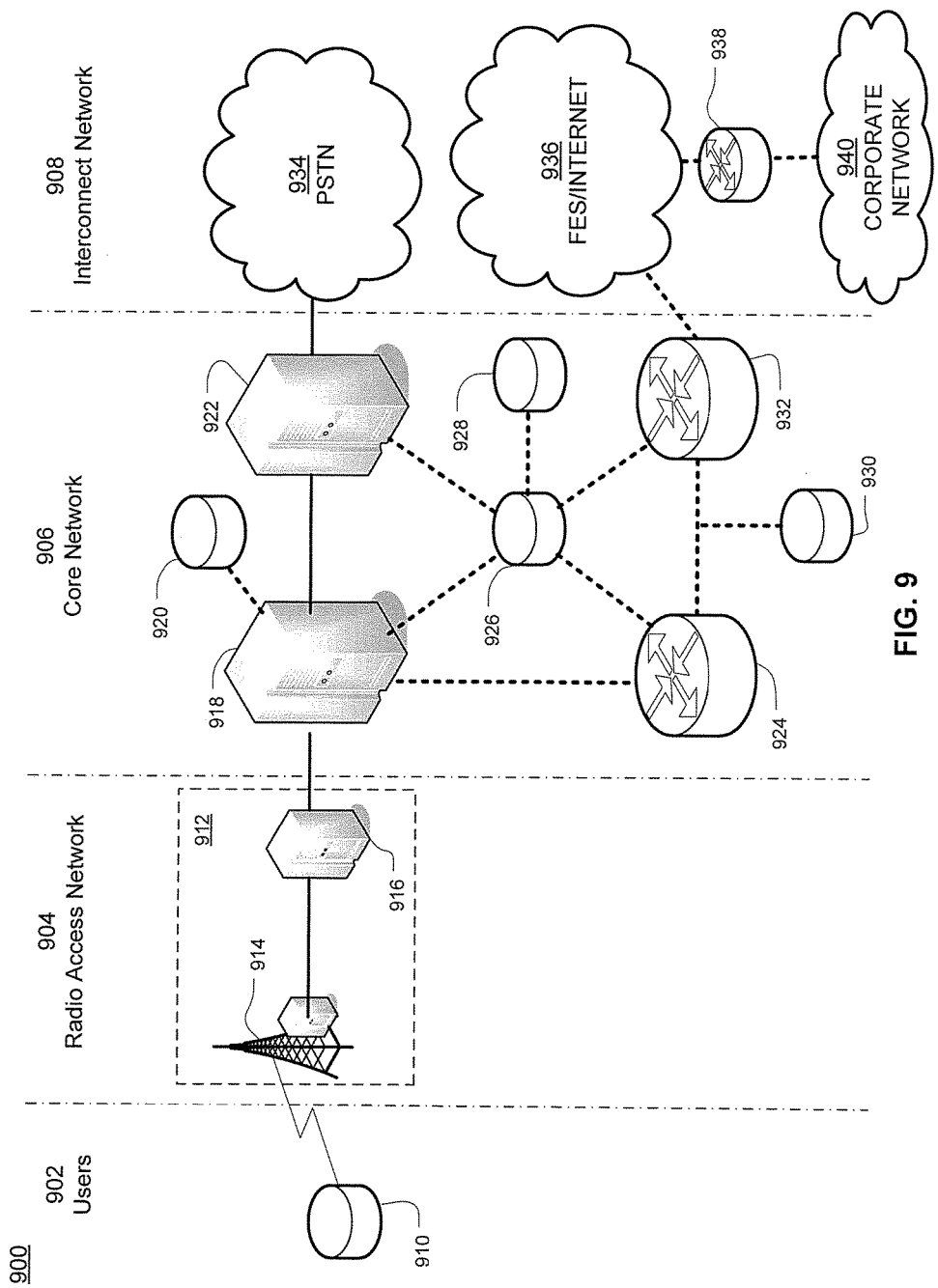
FIG. 9 illustrates an exemplary architecture of a GPRS network.

FIG. 9 illustrates an architecture of a typical GPRS network 900 as described herein. The architecture depicted in FIG. 9 may be segmented into four groups: users 902, RAN 904, core network 906, and interconnect network 908. Users 902 comprise a plurality of end users, who each may use one or more devices 910. Note that device 910 is referred to as a mobile subscriber (MS) in the description of network shown in FIG. 9. In an example, device 910 comprises a communications device (e.g., mobile device 102, mobile positioning center 116, network entity 300, any of detected devices 500, second device 508, access device 604, access device 606, access device 608, access device 610 or the like, or any combination thereof). Radio access network 904 comprises a plurality of BSSs such as BSS 912, which includes a BTS 914 and a BSC 916. Core network 906 may include a host of various network elements. As illustrated in FIG. 9, core network 906 may comprise MSC 918, service control point (SCP) 920, gateway MSC (GMSC) 922, SGSN 924, home location register (HLR) 926, authentication center (AuC) 928, domain name system (DNS) server 930, and GGSN 932. Interconnect network 908 may also comprise a host of various networks or other network elements. As illustrated in FIG. 9, interconnect network 908 comprises a PSTN 934, an FES/Internet 936, a firewall 1138, or a corporate network 940.

An MSC can be connected to a large number of BSCs. At MSC 918, for instance, depending on the type of traffic, the traffic may be separated in that voice may be sent to PSTN 934 through GMSC 922, or data may be sent to SGSN 924, which then sends the data traffic to GGSN 932 for further forwarding.

When MSC 918 receives call traffic, for example, from BSC 916, it sends a query to a database hosted by SCP 920, which processes the request and issues a response to MSC 918 so that it may continue call processing as appropriate.

HLR 926 is a centralized database for users to register to the GPRS network. HLR 926 stores static information about the subscribers such as the International Mobile Subscriber Identity (IMSI), subscribed services, or a key for authenticating the subscriber. HLR 926 also stores dynamic subscriber information such as the current location of the MS. Associated with HLR 926 is AuC 928, which is a database that contains the algorithms for authenticating subscribers and includes the associated keys for encryption to safeguard the user input for authentication.

In the following, depending on context, "mobile subscriber" or "MS" sometimes refers to the end user and sometimes to the actual portable device, such as a mobile device, used by an end user of the mobile cellular service. When a mobile subscriber turns on his or her mobile device, the mobile device goes through an attach process by which the mobile device attaches to an SGSN of the GPRS network. In FIG. 9, when MS 910 initiates the attach process by turning on the network capabilities of the mobile device, an attach request is sent by MS 910 to SGSN 924. The SGSN 924 queries another SGSN, to which MS 910 was attached before, for the identity of MS 910. Upon receiving the identity of MS 910 from the other SGSN, SGSN 924 requests more information from MS 910. This information is used to authenticate MS 910 together with the information provided by HLR 926. Once verified, SGSN 924 sends a location update to HLR 926 indicating the change of location to a new SGSN, in this case SGSN 924. HLR 926 notifies the old SGSN, to which MS 910 was attached before, to cancel the location process for MS 910. HLR 926 then notifies SGSN 924 that the location update has been performed. At this time, SGSN 924 sends an Attach Accept message to MS 910, which in turn sends an Attach Complete message to SGSN 924.

Next, MS 910 establishes a user session with the destination network, corporate network 940, by going through a Packet Data Protocol (PDP) activation process. Briefly, in the process, MS 910 requests access to the Access Point Name (APN), for example, UPS.com, and SGSN 924 receives the activation request from MS 910. SGSN 924 then initiates a DNS query to learn which GGSN 932 has access to the UPS.com APN. The DNS query is sent to a DNS server within core network 906, such as DNS server 930, which is provisioned to map to one or more GGSNs in core network 906. Based on the APN, the mapped GGSN 932 can access requested corporate network 940. SGSN 924 then sends to GGSN 932 a Create PDP Context Request message that contains necessary information. GGSN 932 sends a Create PDP Context Response message to SGSN 924, which then sends an Activate PDP Context Accept message to MS 910.

Once activated, data packets of the call made by MS 910 can then go through RAN 904, core network 906, and interconnect network 908, in a particular FES/Internet 936 and firewall 1138, to reach corporate network 940.

Figure 10:
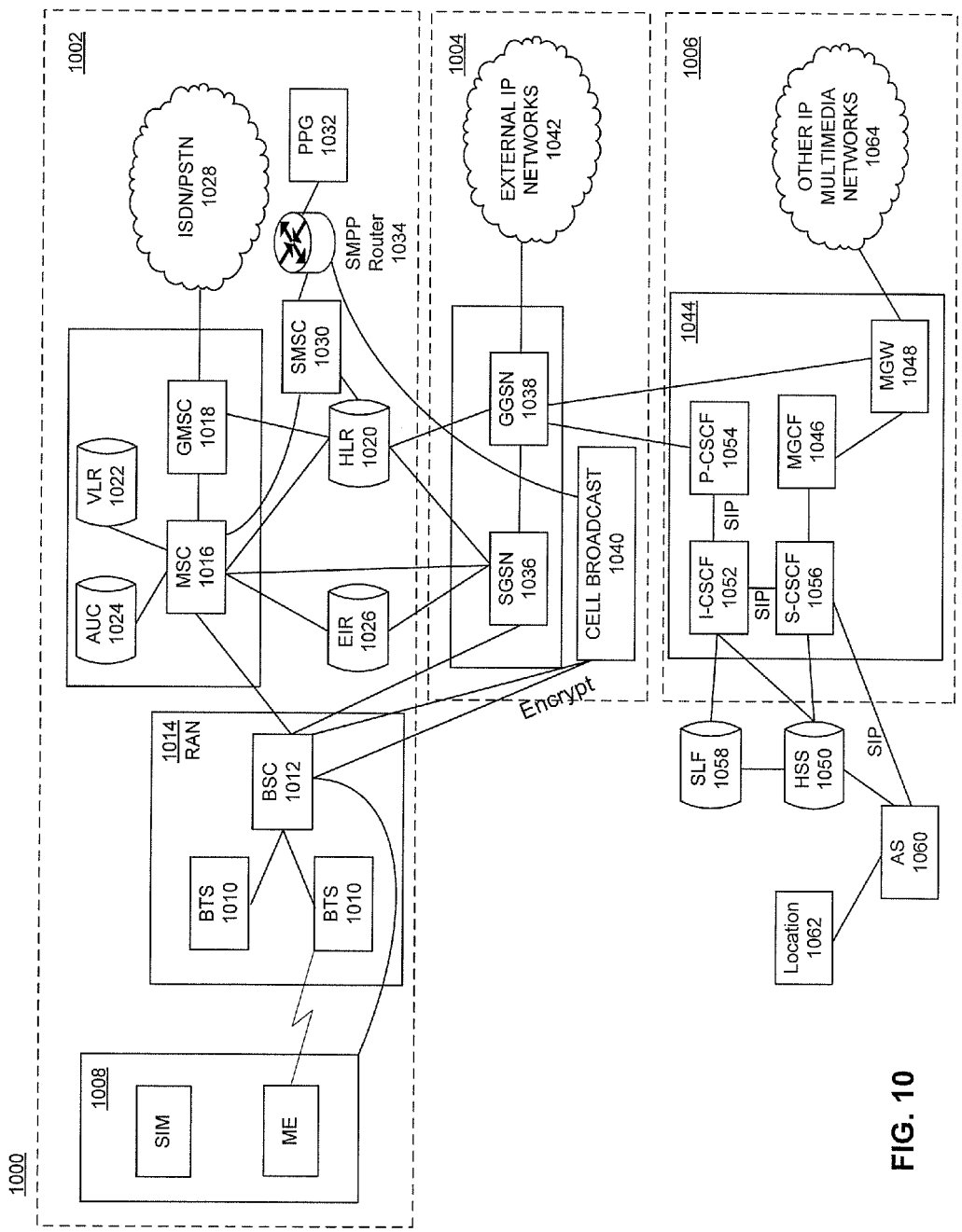
FIG. 10 illustrates an example block diagram view of a global system for mobile communications (GSM)/GPRS/internet protocol (IP) multimedia network architecture.

FIG. 10 illustrates an example block diagram view of a GSM/GPRS/IP multimedia network architecture 1000 as described herein. As illustrated, architecture 1000 includes a GSM core network 1002, a GPRS network 1004 and an IP multimedia network 1006. GSM core network 1002 includes an MS 1008, a BTS 1010, and a BSC 1012. MS 1008 is physical equipment or mobile equipment, such as a mobile phone or a laptop computer that is used by mobile subscribers, with a SIM or a Universal Integrated Circuit Card (UICC). The SIM or UICC includes an IMSI which is a unique identifier of a subscriber. BTS 1010 is physical equipment, such as a radio tower, that enables a radio interface to communicate with MS 1008. Each BTS 1010 may serve more than one MS 1008. BSC 1012 manages radio resources, including BTS 1010. BSC 1010 may be connected to several BTSs 1010. BSC 1012 and BTS 1010 components, in combination, are generally referred to as a BSS or RAN 1014.

GSM core network 1002 also includes a MSC 1016, a GMSC 1018, an HLR 1020, a visitor location register (VLR) 1022, an AuC 1024, and an equipment identity register (EIR) 1026. MSC 1016 performs a switching function for the network. MSC 1016 also performs other functions, such as registration, authentication, location updating, handovers, or call routing. GMSC 1018 provides a gateway between GSM network 1002 and other networks, such as an Integrated Services Digital Network (ISDN) or PSTN 1028. Thus, the GMSC 1018 provides interworking functionality with external networks.

HLR 1020 is a database that contains administrative information regarding each subscriber registered in corresponding GSM network 1002. HLR 1020 also contains the current location of each MS. VLR 1022 is a database that contains selected administrative information from HLR 1020. VLR 1022 contains information necessary for call control and provision of subscribed services for each MS 1008 currently located in a geographical area controlled by VLR 1022. HLR 1020 and VLR 1022, together with MSC 1016, provide the call routing and roaming capabilities of GSM. AuC 1024 provides the parameters needed for authentication and encryption functions. Such parameters allow verification of a subscriber's identity. EIR 1026 stores security-sensitive information about the mobile equipment.

An SMSC 1030 allows one-to-one short message service (SMS) messages to be sent to or from MS 1008. A push proxy gateway (PPG) 1032 is used to "push" (i.e., send without a synchronous request) content to MS 1008. PPG 1032 acts as a proxy between wired and wireless networks to facilitate pushing of data to MS 802. A short message peer-to-peer (SMPP) protocol router 1034 is provided to convert SMS-based SMPP messages to cell broadcast messages. SMPP is a protocol for exchanging SMS messages between SMS peer entities such as short message service centers. The SMPP protocol is often used to allow third parties, e.g., content suppliers such as news organizations, to submit bulk messages.

To gain access to GSM services, such as speech, data, or SMS, MS 1008 first registers with the network to indicate its current location by performing a location update and IMSI attach procedure. MS 1008 sends a location update including its current location information to the MSC 1016/VLR 1022, via BTS 1010 and the BSC 1012. The location information is then sent to HLR 1020 of MS 1008. HLR 1020 is updated with the location information received from the MSC 1016/VLR 1022. The location update also is performed when MS 1008 moves to a new location area. Typically, the location update is periodically performed to update the database as location updating events occur.

GPRS network 1004 is logically implemented on GSM core network 1002 architecture by introducing two packet-switching network nodes, an SGSN 1036, a cell broadcast and a GGSN 1038. SGSN 1036 is at the same hierarchical level as MSC 1016 in GSM network 1002. SGSN 1036 controls the connection between GPRS network 1004 and MS 1008. SGSN 1036 also keeps track of individual MS 1008's locations and security functions and access controls.

A cell broadcast center (CBC) 1040 communicates cell broadcast messages that are typically delivered to multiple users in a specified area. Cell broadcast is one-to-many geographically focused service. It enables messages to be communicated to multiple mobile phone customers who are located within a given part of its network coverage area at the time the message is broadcast.

GGSN 1038 provides a gateway between GPRS network 1002 and a PDN or other external IP networks 1042. That is, GGSN 1038 provides interworking functionality with external networks, and sets up a logical link to MS 1008 through SGSN 1036. When packet-switched data leaves GPRS network 1004, it is transferred to a TCP-IP network 1042, such as an X.25 network or the Internet. In order to access GPRS services, MS 1008 first attaches itself to GPRS network 1004 by performing an attach procedure. MS 1008 then activates a PDP context, thus activating a packet communication session between MS 1008, SGSN 1036, and GGSN 1038.

In a GSM/GPRS network, GPRS services and GSM services can be used in parallel. MS 1008 can operate in one of three classes: class A, class B, and class C. A class A MS can attach to the network for both GPRS services and GSM services simultaneously. A class A MS also supports simultaneous operation of GPRS services and GSM services. For example, class A mobiles can receive GSM voice/data/SMS calls and GPRS data calls at the same time.

A class B MS can attach to the network for both GPRS services and GSM services simultaneously. However, a class B MS does not support simultaneous operation of the GPRS services and GSM services. That is, a class B MS can only use one of the two services at a given time.

A class C MS can attach for only one of the GPRS services and GSM services at a time. Simultaneous attachment and operation of GPRS services and GSM services is not possible with a class C MS.

GPRS network 1004 can be designed to operate in three network operation modes (NOM1, NOM2 and NOM3). A network operation mode of GPRS network 1004 is indicated by a parameter in system information messages transmitted within a cell. The system information messages dictates MS 1008 where to listen for paging messages and how to signal towards the network. The network operation mode represents the capabilities of GPRS network 1004. In a NOM1 network, MS 1008 can receive pages from a circuit switched domain (voice call) when engaged in a data call. MS 1008 can suspend the data call or take both simultaneously, depending on the ability of MS 1008 S. In a NOM2 network, MS 1008 may not receive pages from a circuit switched domain when engaged in a data call, since MS 1008 is receiving data and is not listening to a paging channel. In a NOM3 network, MS 1008 can monitor pages for a circuit switched network while receiving data and vice versa.

IP multimedia network 1006 was introduced with 3GPP Release 5, and includes an IP multimedia subsystem (IMS) 1044 to provide rich multimedia services to end users. A representative set of the network entities within IMS 1044 are a call/session control function (CSCF), a media gateway control function (MGCF) 1046, a media gateway (MGW) 1048, and a master subscriber database, called a home subscriber server (HSS) 1050. HSS 1050 may be common to GSM network 1002, GPRS network 1004 as well as IP multimedia network 1006.

IMS 1044 is built around the call/session control function, of which there are three types: an interrogating CSCF (I-CSCF) 1052, a proxy CSCF (P-CSCF) 1054, and a serving CSCF (S-CSCF) 1056. P-CSCF 1054 is the MS 1008's first point of contact with IMS 1044. P-CSCF 1054 forwards session initiation protocol (SIP) messages received from MS 1008 to an SIP server in a home network (and vice versa) of MS 1008. P-CSCF 1054 may also modify an outgoing request according to a set of rules defined by the network operator (for example, address analysis or potential modification).

I-CSCF 1052 forms an entrance to a home network and hides the inner topology of the home network from other networks and provides flexibility for selecting an S-CSCF 1056. I-CSCF 1052 may contact a subscriber location function (SLF) 1058 to determine which HSS 1050 to use for the particular subscriber, if multiple HSSs 1050 are present. S-CSCF 1056 performs the session control services for MS 1008. This includes routing originating sessions to external networks and routing terminating sessions to visited networks. S-CSCF 1056 also decides whether an application server (AS) 1060 is required to receive information on an incoming SIP session request to ensure appropriate service handling. This decision is based on information received from HSS 1050 (or other sources, such as AS 1060). AS 1060 also communicates to a location server 1062 (e.g., a GMLC) that provides a position (e.g., latitude/longitude coordinates) of MS 1008.

HSS 1050 contains a subscriber profile and keeps track of which core network node is currently handling the subscriber. It also supports subscriber authentication and authorization functions. In networks with more than one HSS 1050, SLF 1058 may provide information on the HSS 1050 that contains the profile of a given subscriber.

MGCF 1046 provides interworking functionality between SIP session control signaling from IMS 1044 and ISUP/BICC call control signaling from the external GSTN networks (not shown). It also controls a MGW 1048 that provides user-plane interworking functionality (e.g., converting between AMR- and PCM-coded voice). MGW 1048 also communicates with other IP multimedia networks 1064.

PoC-capable mobile phones register with the wireless network when the phones are in a predefined area (e.g., job site, etc.). When the mobile phones leave the area, they register with the network in their new location as being outside the predefined area. This registration, however, does not indicate the actual physical location of the mobile phones outside the predefined area.

Figure 11:
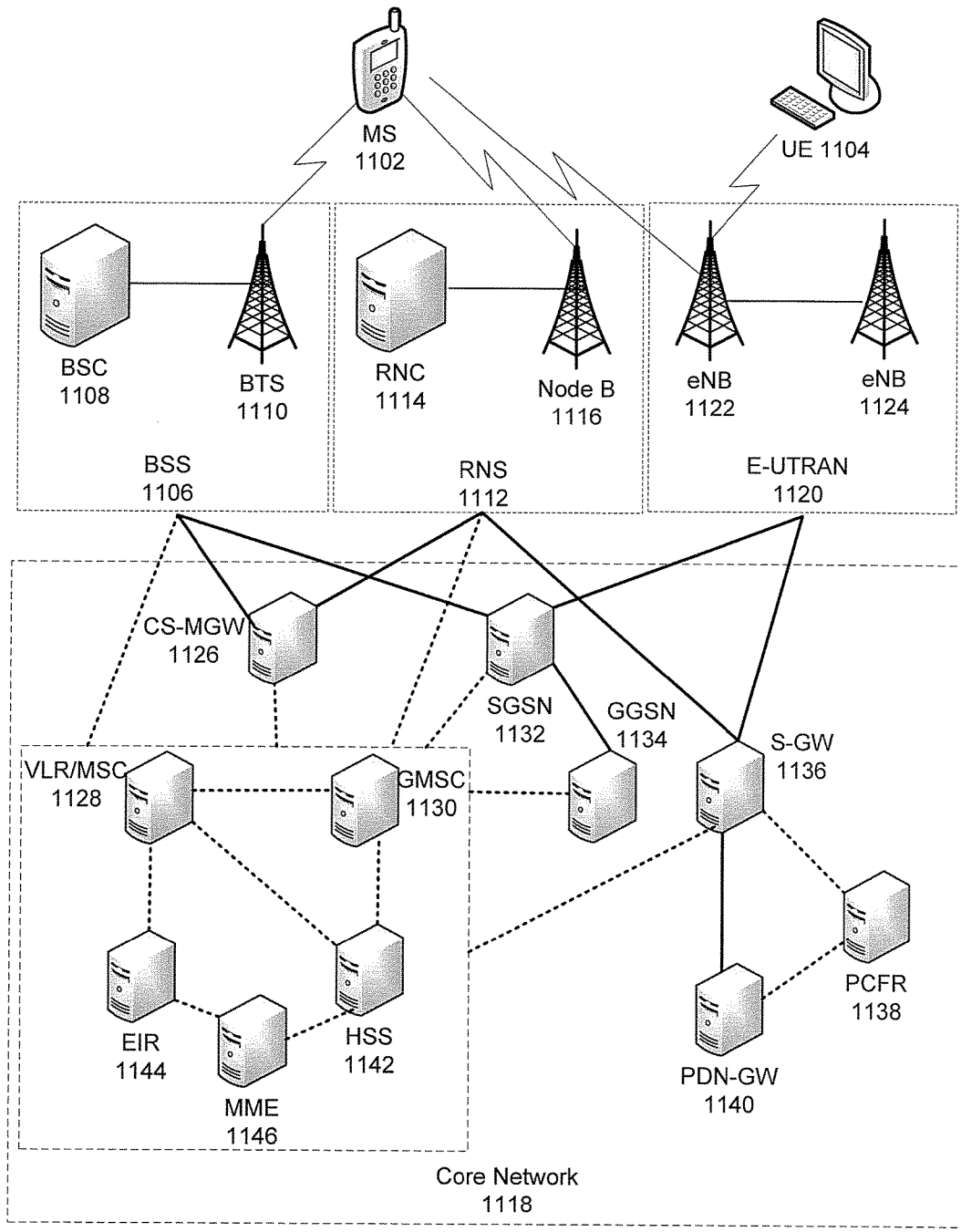
FIG. 11 is a block diagram of an exemplary public land mobile network (PLMN).

FIG. 11 illustrates a PLMN block diagram view of an example architecture that may be replaced by a telecommunications system. In FIG. 11, solid lines may represent user traffic signals, and dashed lines may represent support signaling. MS 1102 is the physical equipment used by the PLMN subscriber. For example, M2M device 108, network entity 300, the like, or any combination thereof may serve as MS 1102. MS 1102 may be one of, but not limited to, a cellular telephone, a cellular telephone in combination with another electronic device or any other wireless mobile communication device.

MS 1102 may communicate wirelessly with BSS 1106. BSS 1106 contains BSC 1108 and a BTS 1110. BSS 1106 may include a single BSC 1108/BTS 1110 pair (base station) or a system of BSC/BTS pairs that are part of a larger network. BSS 1106 is responsible for communicating with MS 1102 and may support one or more cells. BSS 1106 is responsible for handling cellular traffic and signaling between MS 1102 and a core network 1118. Typically, BSS 1106 performs functions that include, but are not limited to, digital conversion of speech channels, allocation of channels to mobile devices, paging, or transmission/reception of cellular signals.

Additionally, MS 1102 may communicate wirelessly with RNS 1112. RNS 1112 contains a Radio Network Controller (RNC) 1114 and one or more Nodes B 1116. RNS 1112 may support one or more cells. RNS 1112 may also include one or more RNC 1114/Node B 1116 pairs or alternatively a single RNC 1114 may manage multiple Nodes B 1116. RNS 1112 is responsible for communicating with MS 1102 in its geographically defined area. RNC 1114 is responsible for controlling Nodes B 1116 that are connected to it and is a control element in a UMTS radio access network. RNC 1114 performs functions such as, but not limited to, load control, packet scheduling, handover control, security functions, or controlling MS 1102 access to core network 1118.

An E-UTRA Network (E-UTRAN) 1120 is a RAN that provides wireless data communications for MS 1102 and user equipment 1104. E-UTRAN 1120 provides higher data rates than traditional UMTS. It is part of the LTE upgrade for mobile networks, and later releases meet the requirements of the International Mobile Telecommunications (IMT) Advanced and are commonly known as a 4G networks. E-UTRAN 1120 may include of series of logical network components such as E-UTRAN Node B (eNB) 1122 and E-UTRAN Node B (eNB) 1124. E-UTRAN 1120 may contain one or more eNBs. User equipment 1104 may be any mobile device capable of connecting to E-UTRAN 1120 including, but not limited to, a personal computer, laptop, mobile device, wireless router, or other device capable of wireless connectivity to E-UTRAN 1120. The improved performance of the E-UTRAN 1120 relative to a typical UMTS network allows for increased bandwidth, spectral efficiency, and functionality including, but not limited to, voice, high-speed applications, large data transfer or IPTV, while still allowing for full mobility.

An example of a mobile data and communication service that may be implemented in the PLMN architecture described in FIG. 11 is EDGE. EDGE is an enhancement for GPRS networks that implements an improved signal modulation scheme known as 8-PSK (phase shift keying). By increasing network utilization, EDGE may achieve up to three times faster data rates as compared to a typical GPRS network. EDGE may be implemented on any GSM network capable of hosting a GPRS network, making it an ideal upgrade over GPRS since it may provide increased functionality of existing network resources. Evolved EDGE networks are becoming standardized in later releases of the radio telecommunication standards, which provide for even greater efficiency and peak data rates of up to 1 Mbit/s, while still allowing implementation on existing GPRS-capable network infrastructure.

Typically MS 1102 may communicate with any or all of BSS 1106, RNS 1112, or E-UTRAN 1120. In a illustrative system, each of BSS 1106, RNS 1112, and E-UTRAN 1120 may provide Mobile Station 1102 with access to core network 1118. Core network 1118 may include of a series of devices that route data and communications between end users. Core network 1118 may provide network service functions to users in the circuit switched (CS) domain or the packet switched (PS) domain. The CS domain refers to connections in which dedicated network resources are allocated at the time of connection establishment and then released when the connection is terminated. The PS domain refers to communications and data transfers that make use of autonomous groupings of bits called packets. Each packet may be routed, manipulated, processed or handled independently of all other packets in the PS domain and does not require dedicated network resources.

The circuit-switched MGW function (CS-MGW) 1126 is part of core network 1118, and interacts with VLR/MSC server 1128 and GMSC server 1130 in order to facilitate core network 1118 resource control in the CS domain. Functions of CS-MGW 1126 include, but are not limited to, media conversion, bearer control, payload processing or other mobile network processing such as handover or anchoring. CS-MGW 1118 may receive connections to MS 1102 through BSS 1106 or RNS 1112.

SGSN 1132 stores subscriber data regarding MS 1102 in order to facilitate network functionality. SGSN 1132 may store subscription information such as, but not limited to, the IMSI, temporary identities, or PDP addresses. SGSN 1132 may also store location information such as, but not limited to, GGSN 1134 address for each GGSN where an active PDP exists. GGSN 1134 may implement a location register function to store subscriber data it receives from SGSN 1132 such as subscription or location information.

Serving gateway (S-GW) 1136 is an interface which provides connectivity between E-UTRAN 1120 and core network 1118. Functions of S-GW 1136 include, but are not limited to, packet routing, packet forwarding, transport level packet processing, or user plane mobility anchoring for inter-network mobility. PCRF 1138 uses information gathered from P-GW 1136, as well as other sources, to make applicable policy and charging decisions related to data flows, network resources or other network administration functions. PDN gateway (PDN-GW) 1140 may provide user-to-services connectivity functionality including, but not limited to, GPRS/EPC network anchoring, bearer session anchoring and control, or IP address allocation for PS domain connections.

HSS 1142 is a database for user information and stores subscription data regarding MS 1102 or user equipment 1104 for handling calls or data sessions. Networks may contain one HSS 1142 or more if additional resources are required. Example data stored by HSS 1142 include, but is not limited to, user identification, numbering or addressing information, security information, or location information. HSS 1142 may also provide call or session establishment procedures in both the PS and CS domains.

VLR/MSC Server 1128 provides user location functionality. When MS 1102 enters a new network location, it begins a registration procedure. A MSC server for that location transfers the location information to the VLR for the area. A VLR and MSC server may be located in the same computing environment, as is shown by VLR/MSC server 1128, or alternatively may be located in separate computing environments. A VLR may contain, but is not limited to, user information such as the IMSI, the Temporary Mobile Station Identity (TMSI), the Local Mobile Station Identity (LMSI), the last known location of the mobile station, or the SGSN where the mobile station was previously registered. The MSC server may contain information such as, but not limited to, procedures for MS 1102 registration or procedures for handover of MS 1102 to a different section of core network 1118. GMSC server 1130 may serve as a connection to alternate GMSC servers for other MSs in larger networks.

EIR 1144 is a logical element which may store the IMEI for MS 1102. User equipment may be classified as either "white listed" or "black listed" depending on its status in the network. If MS 1102 is stolen and put to use by an unauthorized user, it may be registered as "black listed" in EIR 1144, preventing its use on the network. A MME 1146 is a control node which may track MS 1102 or user equipment 1104 if the devices are idle. Additional functionality may include the ability of MME 1146 to contact idle MS 1102 or user equipment 1104 if retransmission of a previous session is required.

As described herein, a telecommunications system wherein management and control utilizing a software designed network (SDN) and a simple IP are based, at least in part, on user equipment, may provide a wireless management and control framework that enables common wireless management and control, such as mobility management, radio resource management, QoS, load balancing, etc., across many wireless technologies, e.g. LTE, Wi-Fi, and future 5G access technologies; decoupling the mobility control from data planes to let them evolve and scale independently; reducing network state maintained in the network based on user equipment types to reduce network cost and allow massive scale; shortening cycle time and improving network upgradability; flexibility in creating end-to-end services based on types of user equipment and applications, thus improve customer experience; or improving user equipment power efficiency and battery life—especially for simple M2M devices—through enhanced wireless management.

While examples of a telecommunications system in which emergency alerts can be processed and managed have been described in connection with various computing devices/processors, the underlying concepts may be applied to any computing device, processor, or system capable of facilitating a telecommunications system. The various techniques described herein may be implemented in connection with hardware or software or, where appropriate, with a combination of both. Thus, the methods and devices may take the form of program code (i.e., instructions) embodied in concrete, tangible, storage media having a concrete, tangible, physical structure. Examples of tangible storage media include floppy diskettes, CD-ROMs, DVDs, hard drives, or any other tangible machine-readable storage medium (computer-readable storage medium). Thus, a computer-readable storage medium is not a signal. A computer-readable storage medium is not a transient signal. Further, a computer-readable storage medium is not a propagating signal. A computer-readable storage medium as described herein is an article of manufacture. When the program code is loaded into and executed by a machine, such as a computer, the machine becomes an device for telecommunications. In the case of program code execution on programmable computers, the computing device will generally include a processor, a storage medium readable by the processor (including volatile or nonvolatile memory or storage elements), at least one input device, and at least one output device. The program(s) can be implemented in assembly or machine language, if desired. The language can be a compiled or interpreted language, and may be combined with hardware implementations.

The methods and devices associated with a telecommunications system as described herein also may be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an device for implementing telecommunications as described herein. When implemented on a general-purpose processor, the program code combines with the processor to provide a unique device that operates to invoke the functionality of a telecommunications system.

While a telecommunications system has been described in connection with the various examples of the various figures, it is to be understood that other similar implementations may be used or modifications and additions may be made to the described examples of a telecommunications system without deviating therefrom. For example, one skilled in the art will recognize that a telecommunications system as described in the instant application may apply to any environment, whether wired or wireless, and may be applied to any number of such devices connected via a communications network and interacting across the network. Therefore, a telecommunications system as described herein should not be limited to any single example, but rather should be construed in breadth and scope in accordance with the appended claims.

What is claimed:

1. A computer-implemented method performed by a processor, the method comprising:
   receiving a detected health characteristic of a user from a biometric sensor;
   determining an amount of insulin available to an insulin pump is insufficient to treat the user, wherein the detected health characteristic of the user is a blood sugar level;
   identifying a medical service for the user based on a request signal received from a mobile device and the amount of insulin and the blood sugar level, the medical service is based on the detected health characteristic of the user, and the medical service having a type;
   identifying a health insurance plan associated with the user;
   determining a location of the mobile device;
   identifying a plurality of medical service providers based on at least the type of medical service;
   identifying insurance plans accepted by each of the plurality of medical service providers;
   determining a plurality of travel times, wherein each of the plurality of travel times is indicative of an estimated time to travel between the location and a provider location of a respective one of the plurality of medical service providers and wherein the plurality of travel times are based on traffic information;
   determining a plurality of estimated wait times for the plurality of medical service providers based on at least data provided by the at least one of the plurality of medical service providers;
   identifying a first subset of the plurality of medical service providers having operating hours for which an estimated arrival time is outside of a predetermined threshold from the associated operating hours;

determining a ranking of the plurality of medical service providers based on whether each of the plurality of medical service providers accepts the health insurance plan, the plurality of travel times, and the plurality of estimated wait times, wherein the ranking excludes the first subset of the plurality of medical providers; and providing patient information related to the blood sugar level to at least one of the plurality of medical service providers.

2. The method of claim 1, wherein the mobile device comprises a monitoring device including the biometric sensor configured to monitor the detected health characteristic of the user and identifying the medical service is based on an output of the monitoring device, and wherein the output is generated in response to a condition of the detected health characteristic.

3. The method of claim 2, wherein the mobile device further comprises a mobile communication device.

4. The method of claim 1, wherein determining the plurality of travel times is further based on a mode of transportation of the user.

5. The method of claim 1, further comprising:
determining each of a plurality of estimated arrival times associated with at least one of the plurality of medical service providers based on a respective one of the plurality of travel times, and
wherein the ranking is further based on whether the estimated arrival time associated with the respective service provider is within a predefined threshold of operating hours associated with the respective medical service provider.

6. The method of claim 1, wherein the estimated arrival time associated with each of the plurality of medical service providers is based on at least one of a public transportation schedule, a vehicle route, a pedestrian route, or traffic information.

7. The method of claim 1, further comprising:
determining a total cost of the medical service at each of the plurality of medical service providers; and
determining a user cost of the medical service at each of the plurality of medical service providers, wherein the user cost is a difference between the total cost and insurance coverage, wherein the insurance coverage is based on whether each of the plurality of medical service providers accepts the insurance plan associated with the device,
wherein the ranking is further based on the user cost at each of the service providers.

8. The method of claim 1, further comprising:
receiving status data related to a medical device, wherein the medical service is further based on the status data.

9. The method of claim 8, wherein the medical device is an insulin pump, and wherein the status data describes an amount of insulin available to the insulin pump.

10. The method of claim 1, further comprising:
suggesting symptoms to a user based on the detected health characteristic of the user; and
receiving a response from the user based on the symptoms suggested,
wherein the medical service is additionally based on the response from the user regarding the symptoms suggested.

11. A device comprising:
a biometric sensor configured to receive a blood sugar level of a user;

a processor;
a communication system communicatively coupled to the processor; and
a non-transitory memory comprising computer readable instructions that, when executed by the processor, cause the processor to effectuate operations comprising:
receiving status data related to an insulin pump associated with the user, wherein the status data includes an amount of insulin available to the insulin pump being insufficient to treat the user;
in response to the amount of insulin, determining a location of a user device associated with the user;
in response to the amount of insulin, providing a medical request indicative of a type of medical service, wherein the type of medical service is based on the blood sugar level and the amount of insulin;
identifying a health insurance plan associated with the user;
based on the user device location, identifying a plurality of medical service providers that provide the type of medical service requested each of the plurality of medical service providers having an estimated wait time and a provider location;
identifying insurance plans accepted by each of the plurality of medical service providers;
for each of the plurality of medical service providers, determining an estimated travel time between the user device location and the respective provider location of the respective one of the plurality of medical service providers, wherein the estimated travel time is based on traffic data;
for each of a first subset, determining estimated arrival time based on at least the respective estimated travel time;
identifying a first subset of the plurality of medical service providers having operating hours for which the estimated arrival time is outside of a predetermined threshold from the associated operating hours;
ranking the plurality of medical service providers based on at least whether each of the plurality of medical service providers accepts the health insurance plan, the estimated wait times, and the estimated travel times associated with each of the plurality of medical service providers, wherein the ranking excludes the first subset of the plurality of medical providers;
and
providing symptoms, the respective estimated arrival time, and a medical history associated with the user to at least one of the plurality of medical service providers.

12. The device of claim 11, the operations further comprising:
receiving from the user device a selection of one of the ranked plurality of medical service providers; and
providing travel directions from the location to the provider location of the selected one of the ranked plurality of medical service providers.

13. The device of claim 12, the operations further comprising:
causing an appointment to be added to an electronic calendar associated with the selected one of the ranked plurality of medical service providers,
wherein the appointment comprises patient information associated with the user device.

14. The device of claim 13, the operations further comprising:

checking in the user remotely for the appointment at the selected one of the ranked plurality of medical service providers.

15. A computer-implemented method stored on a non-transitory computer-readable medium and performed by a processor, the method comprising:
    receiving a blood sugar level of a user from a sensor associated with the user;
    receiving status data related to an insulin pump associated with the user, wherein the status data includes an amount of insulin available to the insulin pump being insufficient to treat the user;
    identifying a medical service for the user based on the blood sugar level and the status data;
    identifying a health insurance plan associated with the user;
    determining a location of the user;
    identifying a plurality of medical service providers based on at least the type of medical service;
    identifying insurance plans accepted by each of the plurality of medical service providers;
    determining a plurality of travel times, wherein each of the plurality of travel times is indicative of an estimated time to travel between the location and a provider location of a respective one of the plurality of medical service providers and wherein the plurality of travel times are based on traffic information;
    determining a plurality of estimated wait times for the plurality of medical service providers based on at least data provided by the at least one of the plurality of medical service providers;
    determining a ranking of the plurality of medical service providers based on whether each of the plurality of medical service providers accepts the health insurance plan, the plurality of travel times, and the plurality of estimated wait times; and
    providing patient information related to the blood sugar level and the status data to at least one of the plurality of medical service providers.

* * * * *